(12) United States Patent
Sowerby et al.

(10) Patent No.: US 7,313,221 B2
(45) Date of Patent: Dec. 25, 2007

(54) RADIOGRAPHIC EQUIPMENT

(75) Inventors: Brian David Sowerby, Kareela (AU); James Richard Tickner, Erskineville (AU)

(73) Assignee: Commonwealth Scientific and Industrial Research Organization, Campbell (AU)

(*) Notice: Subject to any disclaimer, the term of this patent is extended or adjusted under 35 U.S.C. 154(b) by 0 days.

(21) Appl. No.: 10/537,821

(22) PCT Filed: Dec. 10, 2003

(86) PCT No.: PCT/AU03/01641

§ 371 (c)(1),
(2), (4) Date: Dec. 16, 2005

(87) PCT Pub. No.: WO2004/053472

PCT Pub. Date: Jun. 24, 2004

(65) Prior Publication Data

US 2006/0093088 A1    May 4, 2006

(30) Foreign Application Priority Data

Dec. 10, 2002  (AU) .............................. 2002953244
Aug. 29, 2003  (AU) .............................. 2003904713

(51) Int. Cl.
*G01N 23/04* (2006.01)
*G01V 5/14* (2006.01)

(52) U.S. Cl. .................. 378/63; 250/269.3; 250/269.4

(58) Field of Classification Search .. 250/269.1–269.8, 250/370.12; 378/57, 63
See application file for complete search history.

(56) References Cited

U.S. PATENT DOCUMENTS 2,297,416 A *  9/1942  Kallmann et al. ............ 378/63
(Continued)

FOREIGN PATENT DOCUMENTS

EP          0 459 648 A1    12/1991
EP          0 640 848 A1    1/1995

(Continued)

OTHER PUBLICATIONS

Rynes, J., et al., "Gamma-ray and neutron radiography as part of a pulsed fast neutron analysis inspection system," *Nucl. Instr. And Meth. In Phys. Res.*, A 422 (1999) 895-899, In English.

(Continued)

*Primary Examiner*—Edward J. Glick
*Assistant Examiner*—Anastasia S. Midkiff
(74) *Attorney, Agent, or Firm*—Sughrue Mion Pllc.

(57) ABSTRACT

The invention concerns radiographic equipment. The equipment includes a source of substantially mono-energetic fast neutrons produced via the deuterium-tritium or deuterium-deuterium fusion reactions, comprising a sealed-tube or similar generator for producing the neutrons. The equipment further includes a source of X-rays or gamma-rays of sufficient energy to substantially penetrate an object to be imaged and a collimating block surrounding the neutron and gamma-ray sources, apart from the provision of one or more slots emitting substantially fan-shaped radiation beams. Further included is a detector array comprising a multiplicity of individual scintillator pixels to receive radiation energy from the sources and convert the received energy into light pulses, the detector array aligned with the fan-shaped beams emitted from the source collimator and collimated to substantially prevent radiation other than that directly transmitted from the sources reaching the array. Conversion means are included for converting the light pulses produced in the scintillators into electrical signals. Conveying means are included for conveying an object between the sources and the detector array. Computing means are included for determining from the electrical signals the attenuation of the neutrons and the X-ray or gamma-ray beams and to generate output representing the mass distribution and composition of the object interposed between the source and detector array. The equipment further includes a display means for displaying images based on the mass distribution and the composition of the object being scanned.

31 Claims, 20 Drawing Sheets
(8 of 20 Drawing Sheet(s) Filed in Color)

U.S. PATENT DOCUMENTS

| | | | |
|---|---|---|---|
| 3,787,686 A | | 1/1974 | Culver |
| 3,832,545 A | * | 8/1974 | Bartko .................. 376/159 |
| 3,946,226 A | | 3/1976 | Smith, Jr. |
| 4,066,892 A | * | 1/1978 | Givens .................. 376/165 |
| 4,093,854 A | * | 6/1978 | Turcotte et al. ............. 376/118 |
| 4,122,339 A | | 10/1978 | Smith, Jr. et al. |
| 4,314,155 A | * | 2/1982 | Sowerby .................. 250/253 |
| 4,381,449 A | | 4/1983 | Smith, Jr. |
| 4,675,145 A | * | 6/1987 | Kuswa et al. ............. 376/108 |
| 4,760,252 A | | 7/1988 | Albats et al. |
| 4,884,288 A | | 11/1989 | Sowerby |
| 4,942,302 A | | 7/1990 | Koechner |
| 5,076,993 A | | 12/1991 | Sawa et al. |
| 5,089,640 A | * | 2/1992 | Bockmann et al. ......... 549/563 |
| 5,098,640 A | * | 3/1992 | Gozani et al. ............. 376/166 |
| 5,153,439 A | | 10/1992 | Gozani et al. |
| 5,200,626 A | | 4/1993 | Schultz et al. |
| 5,278,418 A | | 1/1994 | Broadhurst |
| 5,313,504 A | * | 5/1994 | Czirr .................. 376/153 |
| 5,406,078 A | | 4/1995 | Jacobson |
| 5,479,023 A | * | 12/1995 | Bartle .................. 250/390.04 |
| 5,481,584 A | * | 1/1996 | Tang et al. ............. 378/98.9 |
| 5,513,439 A | | 5/1996 | Brauer et al. |
| 5,519,225 A | * | 5/1996 | Mohr et al. ............ 250/390.02 |
| 5,557,108 A | | 9/1996 | Tümer |
| 5,594,253 A | | 1/1997 | Bueno et al. |
| 5,838,759 A | * | 11/1998 | Armistead .................. 378/57 |
| RE36,012 E | * | 12/1998 | Loomis et al. ............ 250/269.4 |
| 5,905,806 A | * | 5/1999 | Eberhard et al. ........... 382/100 |
| 5,991,359 A | | 11/1999 | Graham |
| 6,061,469 A | * | 5/2000 | Walterman .................. 382/154 |
| 6,064,063 A | | 5/2000 | Mickael |
| 6,124,590 A | | 9/2000 | Mickael |
| 6,150,655 A | | 11/2000 | Odom et al. |
| 6,236,709 B1 | | 5/2001 | Perry et al. |
| 6,320,193 B1 | | 11/2001 | Morrison et al. |
| 7,027,555 B2 | * | 4/2006 | Proctor .................. 378/57 |
| 2002/0121604 A1 | * | 9/2002 | Katagiri .................. 250/368 |
| 2002/0171042 A1 | | 11/2002 | Chen et al. |
| 2003/0116715 A1 | * | 6/2003 | Homme et al. ........ 250/370.11 |

FOREIGN PATENT DOCUMENTS

| | | |
|---|---|---|
| GB | 1 364 572 | 8/1974 |
| GB | 1 582 589 | 1/1981 |
| IL | 60538 A | 2/1984 |
| NZ | 237767 | 4/1992 |
| RU | 2130623 C1 | 5/1990 |
| RU | 2065156 C1 | 8/1996 |
| RU | 2155975 C2 | 9/2000 |
| SU | 605475 B | 12/1982 |
| SU | 1608526 A1 | 11/1990 |
| WO | WO 96/13839 A1 | 5/1996 |
| WO | WO 97/41422 A1 | 11/1997 |
| WO | WO 00/29873 A1 | 5/2000 |
| WO | WO 00/43760 A2 | 7/2000 |
| WO | WO 02/090956 A2 | 11/2002 |
| WO | WO 03/040713 A1 | 5/2003 |

OTHER PUBLICATIONS

T. Gonzani, "Review of Neutron Based Non-Intrusive Inspection Techniques," Ancore Corporation, In English.

An, J. et al, "Progress on Developing $^{60}$Co Container Inspection Systems", Applied Radiation and Isotopes 58 (2003) pp. 315-320.

Barzilov, A.P., et al, "NELIS—A Neutron Elemental Analysis System of Commodities of Pallets", (2001) Office of National Drug Control Policy International Symposium.

Brzosko, J.S. et al, "Advantages and Limitations of 14-McV Neutron Radiography", Nuclear Instruments and Methods B72 (1992) pp. 119-131.

Buffler, A. "Contraband Detection by Fast Neutron Scattering", 2$^{nd}$ National Nuclear Technology Conference, NAC, South Africa, May 13-15, 2001, paper D-03.

Chen, G. and Lanza, R.C., "Fast Neutron Resonance Radiography for Elemental Mapping", Final Research Co-ordination Meeting on "Bulk Hydrogen Analysis Using Neutrons", Cape Town, South Africa, Oct. 23-26, 2000, pp. 31-38.

Dokhale, P.A., et al, "NELIS—An Illicit Drug Detection System", AIP Conference Proceedings, 576 (2001) pp. 1061-1064.

Gozani, T. "Neutron Based Non-Intrusive Inspection Techniques", Proc. Internat. Conf. on Neutrons in Research and Industry, Crete, Greece, Jun. 9-15, 1996, SPIE Proceedings Series 2867 (1997) 174-181.

Hussein, E. "Detection of Explosive Materials Using Nuclear Radiation: A Critical Review", SPIE, vol. 1736 (1992) pp. 130-137.

Klann, R.T., "Fast Neutron (14.5 MeV) Radiography: A Comparative Study", 5$^{th}$ World Conference on Neutron Radiograph, Berlin, Jun. 17-20, 1996, 469-483.

Lefevre, H.W., et al "Using a Fast Neutron Spectrometer System to Candle Luggage for Hidden Explosives", Proc. Internat. Conf. on Neutrons in Research and Industry, Crete, Greece, Jun. 9-15, 1996, SPIE Proceedings Series 2867 (1997) pp. 206-210.

Le Tourneur, P. et al, "Neutron Fan Beam Source for Neutron Radiography Purpose", 15$^{th}$ Int. Conf. on Applications of Accelerators in Research and Industry, Denton, Texas, USA, Nov. 4-7, 1998.

Mikerov, V.I. et al, "Investigation of Prospects of Fast Neutron Radiography on the Basis of Portable Equipment", IAEA Coordinated Research Programme on "Bulk Hydrogen Analysis Using Neutrons", Cape Town, South Africa, Oct. 23-26, 2000, Report F1-RC-655.3.

Millen, M. J., et al, "Plant Trial of a Fast Neutron and Gamma-Ray Transmission Gauge for the On-belt Determination of Moisture in Lump Coke", Nuclear Geophysics 4 (1990) 215-226.

Rynes, J. et al, "Gamma-ray and Neutron Radiography as Part of a Pulsed Fast Neutron Analysis Inspection System", Nuclear Instruments and Methods A422 (1999) pp. 895-899.

Tickner, J.R. et al, "A Detection System", Australian Provisional Patent Application No. 2002/2953,244, filed Dec. 10, 2002.

* cited by examiner

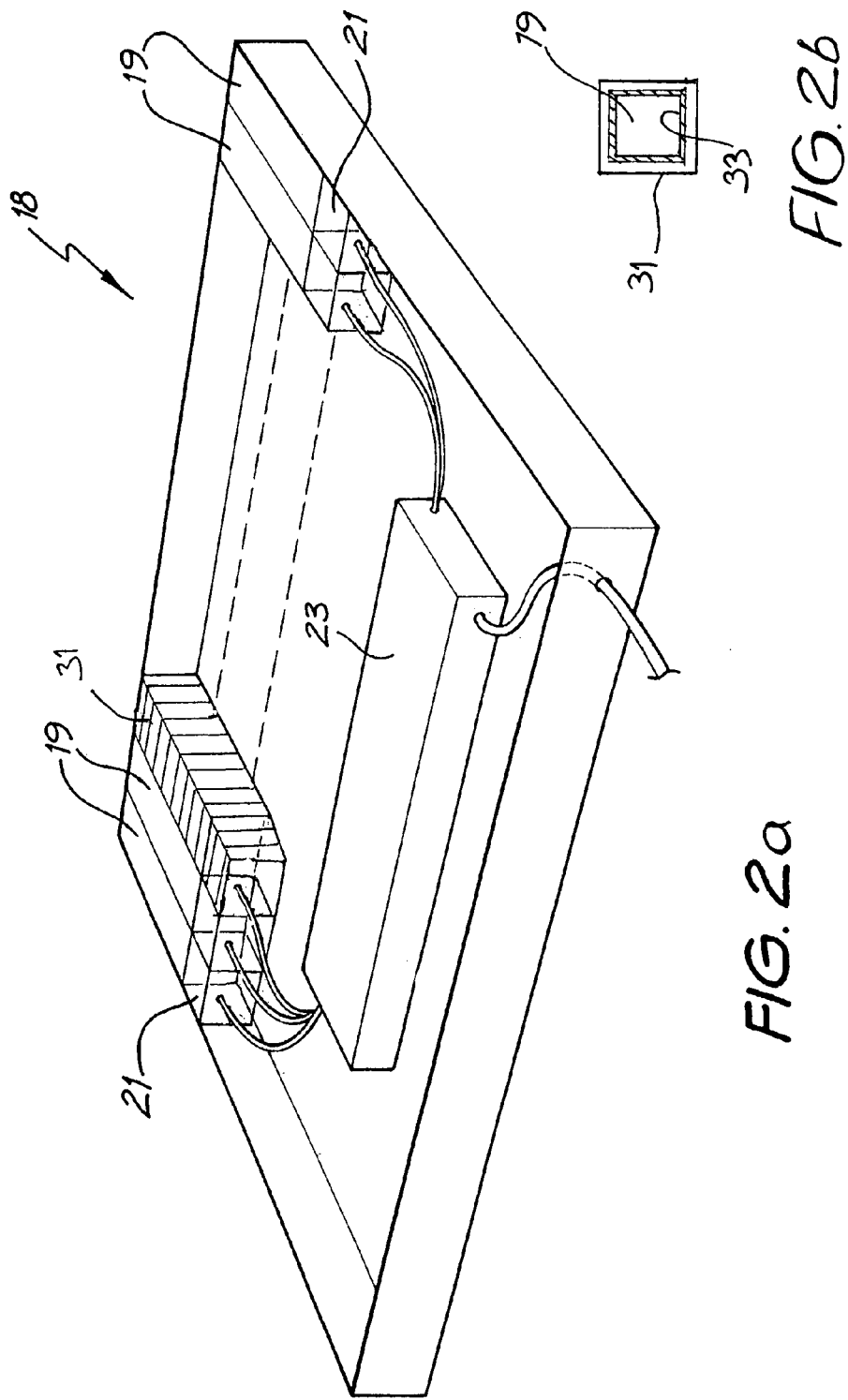

RADIOGRAPHIC EQUIPMENT

This application is a 371 of PCT/AU2003/001641, filed Dec. 10, 2003; the disclosure of which is incorporated herein by reference.

TECHNICAL FIELD

This invention concerns radiographic equipment. In particular the invention concerns radiographic equipment for the detection of concealed articles, substances and materials. For instance, the invention may be applied to the detection of concealed weapons, explosives, contraband, drugs and other articles, substances and materials in items such as aircraft baggage, airfreight or shipping containers.

BACKGROUND ART

Technologies based on X-rays, gamma-rays and neutrons have been proposed to tackle this problem (Hussein, E., 1992, Gozani, T., 1997, An, J. et al, 2003). The most widely adopted technology is the X-ray scanner which forms an image of an item being examined by measuring the transmission of X-rays through the item from a source to a spatially segmented detector. X-rays are most strongly attenuated by dense, higher atomic number materials such as metals. Consequently, X-ray scanners are ideal for detecting items such as guns, knives and other weapons. However, X-rays provide little discriminating power between organic and inorganic elements. Using X-rays the separation of illicit organic materials such as explosives or narcotics from commonly found, benign organic materials is not possible.

An elemental identification system is being developed for the inspection of commodities shipped on pallets. The system called NELIS (Neutron Elemental Analysis System) utilises a 14 MeV neutron generator and three gamma ray detectors to measure induced gamma rays from the cargo (Dokhale, P. A. et al, 2001; Barzilov, A. P., Womble, P. C. and Vourvopoulos, G., 2001). NELIS is not an imaging system and is used in conjunction with an X-ray scanner to help identify gross composition anomalies.

A Pulsed Fast Neutron Analysis (PFNA) cargo inspection system has been developed (Gozani, T., 1997, Sawa et al., 1991) and commercialised through Ancore Corporation. The PFNA system uses a collimated beam of nanosecond-pulsed fast neutrons and the resulting spectrum of gamma rays is measured. The PFNA method allows the ratios of key organic elements to be measured. The nanosecond-pulsed fast neutrons are required in order to localise the specific regions contributing to the measured gamma-ray signal by time-of-flight spectrometry. In practice the technique is limited by the very expensive and complex particle accelerator, the limited neutron source strength and low gamma-ray detection efficiency and the resulting slow scan speeds.

Neutron radiography systems have the advantage of direct measurement of transmitted neutrons and are therefore more efficient than techniques measuring secondary radiation such as neutron-induced gamma rays. Fast neutron radiography has the potential to determine the line-of-sight 'organic image' of objects (Klann, 1996). In contrast to X-rays, neutrons are most strongly attenuated by organic materials, especially those with high hydrogen contents.

A fast neutron and gamma ray and radiography system has been developed by Rynes et al (1999) to supplement PFNA. In this system nanosecond-pulsed fast neutrons and gamma rays from an accelerator are transmitted through the object and the detected neutron and gamma ray signals are separated by arrival time. The resulting system is claimed to combine the advantages of both X-ray radiography and PFNA systems. However it is limited by the very expensive and complex particle accelerator.

Bartle (1995) has suggested using the fast neutron and gamma-ray transmission technique (Millen et al, 1990) to detect the presence contraband in luggage, etc. However this technique has not been used for imaging and its practical application to contraband detection has not been investigated.

Mikerov, V. I. et al, (2000) have investigated the possibility of fast neutron radiography using a 14 MeV neutron generator and luminescent screen/CCD camera detection system. Mikerov found that applications were limited by both the low detection efficiency of the 2 mm thick luminescent screen for fast neutrons and the high sensitivity of the screen to X rays produced by the neutron generator.

Neutron radiography systems using a 14 MeV generator and thermal neutron detection are commercially available (Le Tourneur, P., Bach, P. and Dance, W. E., 1998). However the fact that the fast neutrons are slowed down (thermalised) prior to performing radiography limits the size of the object being imaged to a few cm. No fast neutron radiography systems are commercially available that involve fast neutron detection.

Most work conducted with neutron radiography has been conducted in the laboratory using neutrons from nuclear reactors or particle accelerators that are not suited to a freight-handling applications (Lefevre, H. W, et al, 1996, Miller, T. G., 1997, Chen, G. and Lanza, R. C., 2000, Brzosko, J. S. et al, 1992).

To improve the ability of fast neutron radiography systems to provide discrimination between various organic materials, systems using multiple neutron energy sources, together with detectors with the means for distinguishing between the different neutron energies have been proposed (Chen, G. and Lanza, R. C., 2000, Buffler, 2001). The key drawbacks of these systems have been their reliance on complex, energy-discriminating neutron detectors and/or their use of sophisticated, high-energy accelerator-based neutron sources.

Perion et al. (Perion, 2000) have proposed a scanner using a high-energy (MeV) X-ray Bremsstrahlung or radioisotope source. By either modulating the average source energy by rapidly inserting and removing a low atomic number filter, or by measuring the energy of detected X-rays, it is possible to measure transmission through the object being scanned over two different X-ray energies, one where Compton scattering dominates and one where pair-production is significant. This information can be used to deduce the density and average atomic number of material in each pixel of the scan image. The main drawback of this scheme is the low contrast between different elements, even when very high energy X-ray sources are used. The cost of the Perion detector array would also be very high. Alternatively, Perion suggests that measurement of the transmission of both X-rays and neutrons (produced either directly in the Bremsstrahlung target or by inserting a neutron-producing filter) can yield similar information. The main disadvantage of this method is the low energy of neutrons produced via (gamma, n) reactions. This limits the ability of the neutrons to penetrate through thick cargoes and increases the difficulty in adequately detecting the transmitted neutrons. In particular, it is unlikely that the disclosed stacked scintillator detector would be able to distinguish neutrons in the presence of a much more intense X-ray beam. A disadvantage of both the dual energy X-ray and the X-ray/neutron schemes is that the X-rays and neutrons cover a wide range of energies. This means that it is not possible to model transmission using a simple exponential relation and that it is not straightforward to extract quantitative cross-section information that could be used for material identification.

DISCLOSURE OF INVENTION

The present invention is radiographic equipment comprising:

a source of substantially mono-energetic fast neutrons produced via the deuterium-tritium or deuterium-deuterium fusion reactions, comprising a sealed-tube or similar generator for producing the neutrons;

a source of X-rays or gamma-rays of sufficient energy to substantially penetrate an object to be imaged;

a collimating block surrounding the neutron and X-ray and gamma-ray sources, apart from the provision of one or more slots for emitting substantially fan-shaped radiation beams;

a detector array comprising a multiplicity of individual scintillator pixels to receive radiation energy emitted from the sources and convert the received energy into light pulses, the detector array aligned with the fan-shaped radiation beams emitted from the source collimator and collimated to substantially prevent radiation other than that directly transmitted from the sources reaching the array;

conversion means for converting the light pulses produced in the scintillators into electrical signals;

conveying means for conveying the object between the sources and the detector array;

computing means for determining from the electrical signals the attenuation of the neutrons and the X-ray or gamma-ray beams and to generate output representing the mass distribution and composition of the object interposed between the sources and detector array; and display means for displaying images based on the mass distribution and the composition of the object being scanned.

An advantage of the present invention is that the neutrons are essentially mono-energetic. Hence it is possible to model the neutron transmission using a simple exponential relation and moreover, information is more accurately obtained which is useful for material identification.

The equipment according to at least one embodiment of the invention has the added advantage of direct measurement of transmitted neutrons and is therefore much more efficient when compared with prior art systems which measure secondary radiation such as neutron-induced gamma rays.

The radiographic equipment may utilise one or more neutron energies. In an example of a dual neutron energy technique, the radiographic equipment may utilise two tubes, one to produce substantially 14 MeV neutrons via the deuterium-tritium fusion reaction and a second to produce substantially 2.45 MeV neutrons via the deuterium-deuterium fusion reaction. The measurement of the neutron transmission at a second energy can be used to enhance the capability of the single energy transmission technique.

The source of X-rays or gamma-rays may comprise a radioisotope source such as $^{60}Co$ or $^{137}Cs$ with energy sufficient to substantially penetrate through the object to be imaged. The $^{60}Co$ or $^{137}CS$ source may have an energy of about 1 MeV although other energies may be used depending on the source. Alternatively an X-ray tube, or an electron linear accelerator to produce Bremsstahlung radiation could be used.

Collimation of both the source of X-rays or gamma-rays and the source of neutrons, advantageously acts to minimise scattering. Furthermore, appropriate collimation of both the sources and detector ensures a narrow beam geometry and therefore greater accuracy when determining the attenuation of neutrons and gamma rays through an object. Moreover, the highly collimated fan-shaped beam provides increased radiation safety. The collimating block may be manufactured from thick paraffin, thick concrete, iron-shot concrete shielding blocks, steel, lead, or the like. Similarly, the or each detector array may be housed within a detector shielding having a slot in order to provide the collimation. The detector collimation shielding may be made from iron and may have a thickness of greater than about 100 mm. The width of the slot may be selected to allow direct passage of neutrons and gamma rays from the source to the detector and to shield the detector array from scattered radiation. The detector slot may be about the same width as the detector array. The source collimator slots may be narrower.

The detector array may comprise one or more columns of scintillator pixels.

The same detector array may be able to sense both neutrons and X-rays or gamma rays. Energy discrimination may be used to distinguish the signals or the detector can operate sequentially on the neutrons and X-rays or gamma rays. An advantage of using the same detector array to sense neutrons and X-rays or gamma rays, is that a reduction in the cost of the detector array may be achieved.

Optionally, separate detector arrays may be used to respectively sense the neutrons and X-rays or gamma rays, with or without separate neutron and X-ray or gamma-ray detector collimators.

The scintillators may be selected such that their spectral response is closely matched to the photodiodes. The scintillators may further be surrounded by a mask to cover at least a portion of each of the scintillators, each mask having a first reflective surface to reflect escaped light pulses back into the scintillator. The mask will have an opening to allow scintillator light to be detected by the photodiode. The mask may comprise layers of PTFE tape and/or Tyvek paper. Advantageously, the efficiency of plastic scintillators with a mask for neutrons may be greater than 10%. The material surrounding the scintillators acts to ensure that light which escapes the scintillators is reflected back to be detected. In an example where each detector array includes orange-light emitting plastic scintillators and silicon photodiodes, the equipment may advantageously have a higher performance efficiency allowing images to be collected more quickly. Moreover, the equipment may be manufactured at a relatively cheaper cost.

Silicone oil, GE-688 grease, polysiloaxine, optical cement such as Eljen EJ-500 cement, or the like may be used to optically couple the photodiodes to the respective scintillators.

Where the radiographic equipment comprises a single detector array for sensing both neutrons and X-rays or gamma rays, the scintillators may be plastic scintillators or liquid scintillators.

In a further example where the radiographic equipment comprises dual neutron sources and a source of X-rays or gamma-rays, the scintillators may be plastic or liquid scintillators. In this example, the scintillators may be coupled to photomultiplier tubes.

Where the radiographic equipment comprises separate neutron and gamma-ray detector arrays, the neutron scintillators may be preferentially plastic scintillators or liquid scintillators and the gamma-ray scintillators may be plastic scintillators, liquid scintillators or inorganic scintillators such as caesium iodide, sodium iodide or bismuth germanate. Alternatively the X-ray or gamma ray detectors may be ionisation chambers.

The radiation receiving face of each scintillator, or the 'area' of each scintillator, corresponds to a single pixel. The area of each scintillator may typically be smaller than about 20 mm by 20 mm. Smaller areas lead to improved spatial resolution.

The thickness of each scintillator may be in the range 50 to 100 mm and may be a function of the detection efficiency and light collection efficiency. In an example where the object to be imaged is a unit load device or ULD such as those typically used in airport environments, the radiation receiving face of the array of scintillators may have dimensions of about 120 mm×3300 mm and may comprise about 1000 pixels. When combined with a 14 MeV neutron source energy of approximately $10^{10}$ neutrons/second, the contents of a single ULD may be imaged over a time period of about one minute.

Alternatively separate neutron and gamma-ray scintillators may be used, comprising, for example, about 1000 neutron pixels and about 500 gamma ray pixels. In practice the gamma ray pixels may be made smaller than the neutron pixels which advantageously provides high-resolution spatial images.

In a further example, the conversion means may comprise photomultiplier tubes and wavelength shifting optical fibres (WSF). In this example, light from a row or column of scintillator rods may be collected by the WSF and transmitted to a multi-anode photomultiplier tube. By indexing the row and column producing the light pulse, the scintillator rod intercepting the radiation maybe inferred.

The conversion means may include low noise and high gain amplifiers to amplify the output signals. The conversion means may include a computer to perform image processing and display the images to an operator on a computer screen.

The detector may be temperature controlled to reduce noise and improve stability. For instance, the photodiodes and preamplifiers may be cooled to about −10° C. or lower.

In one example, as an object to be imaged is scanned, one or more outputs are obtained measuring the transmission of, for instance, the 14 MeV neutrons through the object and the transmission of the 1 MeV X-ray or gamma-rays through the object. For dual energy neutron scanning, the transmission of say the 2.45 MeV neutrons through the object is also measured. The invention is not limited to the use of these energies alone.

Where a single detector array is used for receiving radiation energy from the source of X-rays or gamma rays and the source of neutrons, the object may be scanned more than once.

Where separate detectors are used for receiving radiation energy from the source of neutrons and the source of X-rays or gamma rays, the output signal may comprises a first output from the first array of scintillators and a second output from the second array of scintillators, where the first output is related to the neutron count rate in each pixel location of the detector, and the second output is related to the X-ray or gamma-ray count rate in each pixel location of the detector.

Each of the source inputs may be separately processed. A simple scintillation spectrum may be collected separately for each pixel of the array to deduce neutron and X-ray or gamma-ray count rates for each pixel. The information may then be assembled to form a complete 2-dimensional neutron image and a complete 2-dimensional X-ray or gamma-ray image. The resulting image may have a vertical resolution governed by the pixel size, and a horizontal resolution governed by the pixel size and the frequency with which the array is read out.

The computer may also be able to perform automatic material identification. For instance, the transmission outputs may be converted to mass-attenuation coefficient images for each pixel for display on a computer screen with different pixel values mapped to different colours. In particular mass-attenuation coefficient images may be obtained from the count rates measured from the transmissions for each of the 14 MeV neutrons and X- or gamma-rays or the 14 MeV neutrons, 2.45 MeV neutrons and X- or gamma-rays.

Analysis of the mass-attenuation coefficient images allows a variety of inorganic and organic materials to be distinguished. Such analysis may include forming cross section ratio images between pairs of mass attenuation coefficient images. Depending on whether a single or dual neutron sources are utilised, cross section ratio images may be formed from the mass-attenuation coefficient images of the source of neutrons and the X-rays or gamma-rays, or the first and second sources of neutrons and the first or second source of neutrons and the X-rays or gamma-rays. For example, the 14 MeV neutrons and the X-rays or gamma-rays, the 14 MeV neutrons and the 2.45 MeV neutrons, and the 2.45 MeV neutrons and the X-rays or gamma-rays. Advantageously, such ratios are independent of the mass of the object.

The proportions in which the cross section ratio images are combined may be operator adjusted to maximise contrast and sensitivity to a particular object being examined in the image.

An image may be formed that is a linear combination of two cross section ratio images.

Two regions in an image may be identified which contain a first substance, but only one of the regions may contain a second substance. By performing cross section subtractions the image of the first substance may be effectively removed leaving the image of the second substance available for identification. The mass of the second substance may be obtained from the X- or gamma-ray transmission data.

In one example, the source of neutrons and the detector are stationary and the conveyance means is arranged such that the object is moved in front of the source of neutrons and gamma rays. In a further example, the object may be stationary and the conveyance means arranged such that the source and the detector move in synchronicity either side of the object. In a still further example, multiple sets of detectors may be situated around sources which are centrally located to allow scans of a plurality of separate objects to be acquired simultaneously. This would have the advantage of improving throughput. In such an example, the conveyance means may be arranged such that the objects can be moved between the source of neutrons and the respective detector. Alternatively, the sources and detectors can be rotated around the object to be examined to allow multiple views to be obtained.

The rate at which the object is able to be moved in front of either the source of neutrons, or, the source of neutrons and X-rays or gamma-rays is partially dependent on the intensity of the neutron and gamma ray sources. The intensity of the single neutron source of 14 MeV may be in the order $10^{10}$ neutrons/second, or as high as practically possible in order to improve counting statistics.

The rate at which the object is able to be moved in front of the source of neutrons and X-rays or gamma-rays is further dependent on the radiation receiving face of the array of scintillators and the number of scintillators. In addition, the length of the array is partially dependent on the length of the object to be imaged.

The object may be scanned between the neutron and gamma ray sources and detector and may pass through a shielded tunnel. The conveyance means may comprise a pair of rails for the positioning of a dolly or platform on which the object may be transported. Alternatively, the conveyance means may include a conveyor belt or other like arrangement for passing or winching objects through the tunnel. The conveyance means may be automated such that the object is smoothly transported in front of the source of neutrons at a controllable uniform rate.

The invention may be applied to non-invasive examination of sea cargo, air cargo Unit Load Devices (ULD), or smaller containers or packages, the detection of contraband, explosives and other articles, substances and materials. It may provide improved specificity for contraband materials, such as organic materials in primarily inorganic matrices, as well as the detection and identification of specific classes of organic material. It is particularly suited for the detection of explosives, narcotics and other contraband items concealed in aircraft baggage, airfreight containers and shipping containers.

A further advantage of at least one embodiment of the invention is that use of a neutron generator for producing neutrons is able to be switched on and off.

It may also provide increased automation of the inspection process, with reduced reliance on human operators.

Further, it may provide a fast scanning rate so that a high throughput can be achieved. It is simple, low-cost and uses safe radiation sources; and simple, low-cost radiation detection systems. It may operate with a high detection rate and low false alarm probability.

BRIEF DESCRIPTION OF DRAWINGS

The patent or application file contains at least one drawing executed in color. Copies of this patent or patent application publication with color drawing(s) will be provided by the Office upon request and payment of the necessary fee.

Several examples of the invention will now be described with reference to the accompanying drawings, in which:

FIG. 1b is a perspective view of a portion of the radiographic equipment shown in FIG. 1a;

FIG. 2a is a schematic illustration of one module of the radiographic equipment's detector array;

FIG. 2b is an end view of a scintillator illustrated in the detector array shown in FIG. 2a, where the scintillator is surrounded by a mask having a first reflective surface;

BEST MODE FOR CARRYING OUT THE INVENTION

Figure 1A:
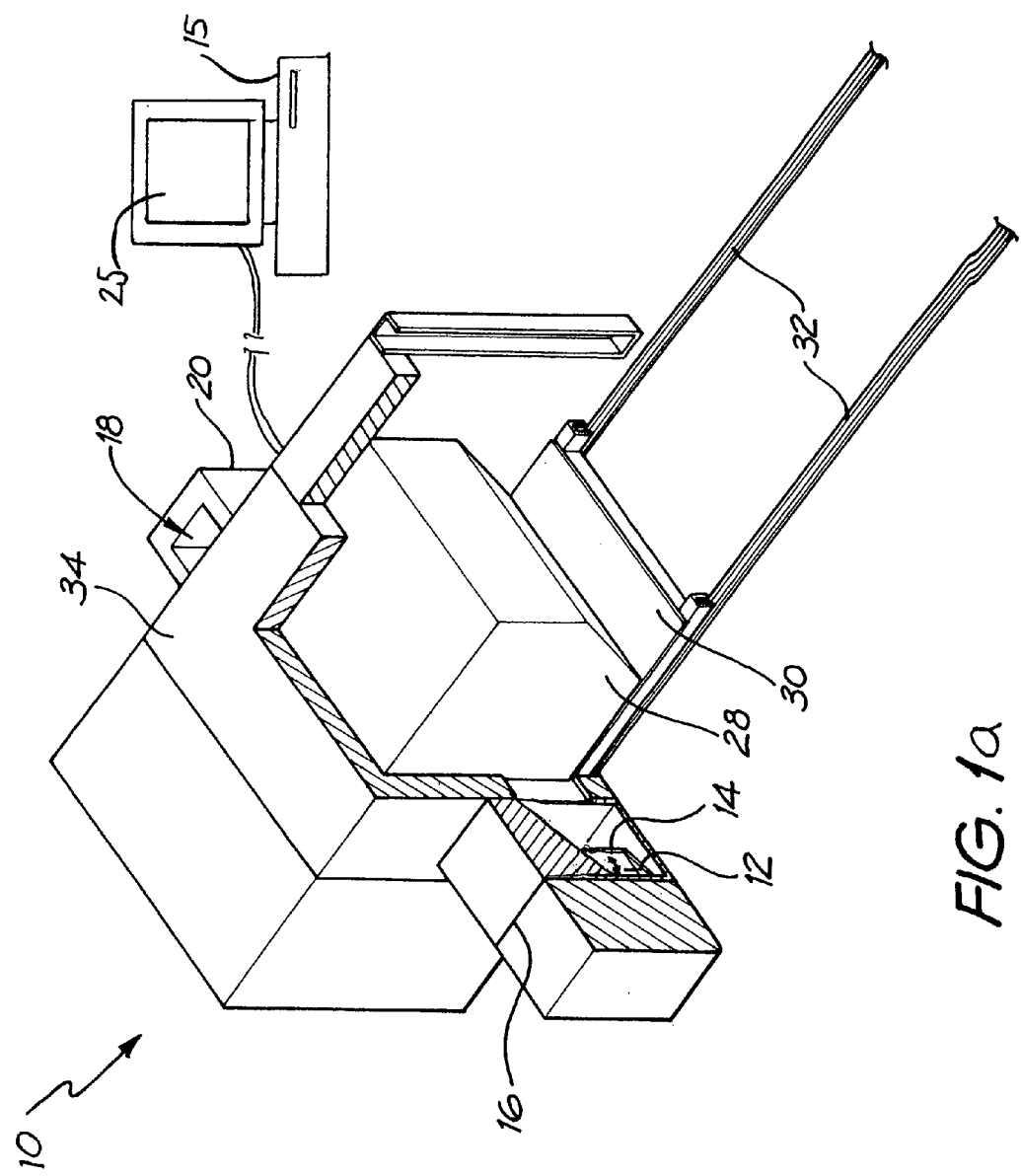
FIG. 1a is a perspective view of an example of the radiographic equipment.

FIG. 1a illustrates the general layout of the radiographic equipment 10. The equipment 10 includes two separate generators of radiation, the first is an A-325 MF Physics neutron generator having a D-T neutron emitting module to produce a neutron energy source 12 having an energy of 14 MeV. The neutron generator is operated at a voltage of 80-110 kV. The second generator of radiation is a 0.82 GBq (or 22 mCi) $^{60}$Co source 14 to produce a source of gamma-rays and is located to the right of and adjacent to the neutron generator. The neutron generator and $^{60}$Co source 14 are situated within a collimating block in the form of a source shield housing 16.

Figure 2C:
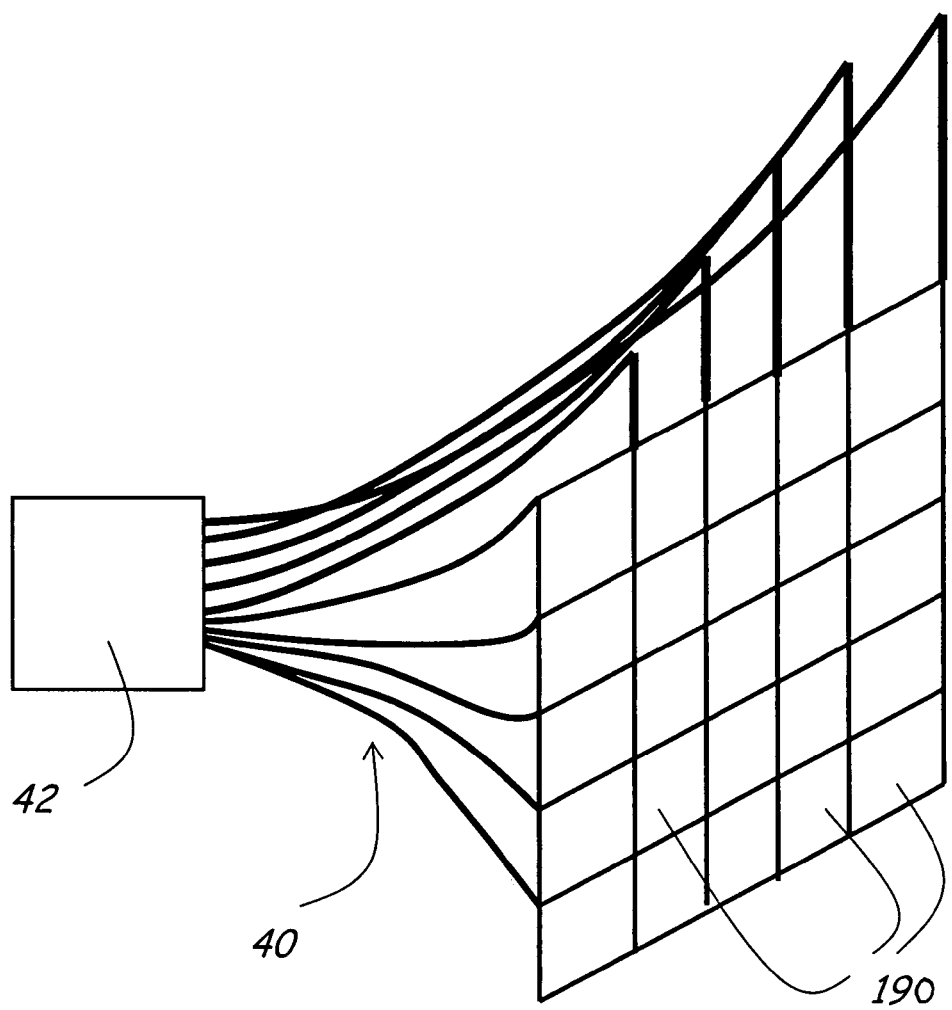
FIG. 2c is a schematic illustration of a further variation of the radiographic equipment's detector array.

A 1600 mm long and 20 mm wide detector array 18 is situated in the vicinity of the radiation source and is housed in a detector shield housing 20. The detector array 18, more clearly shown in FIG. 2a is built up of eighty plastic scintillator rods 19 (of which only a portion are shown), each with a radiation receiving area of 20 mm×20 mm, and a length of 75 mm. The radiation receiving area of each scintillator rod 19 corresponds to a single pixel in the image-frame. The term image frame is used to describe the two-dimensional array containing the number of counts measured in each pixel, accumulated over a fixed time interval. The scintillator rods 19 are made of an orange plastic scintillator in order to match the spectral response of the silicon photodiodes 21 to the respective plastic scintillators. The photodiodes 21 are optically coupled to respective scintillators 19 with optical cement. A reflective mask 31 (of which only one is illustrated) is painted on each of the orange scintillator rod and photodiode combinations to minimise the loss of any light that escapes the scintillator rods. As illustrated in FIG. 2b, each mask 31 has a first reflective surface 33 to reflect escaped light pulses back into the scintillator 19.

In the primary embodiment, the scintillation light produced in a rod 19 by an incident neutron or X- or gamma-ray is detected by a photodiode 21 attached to the end of the rod 19. In a first variation, light from a row or column of scintillator rods is collected by a wavelength shifting optical fibre and transmitted to the photodiode. By indexing the row and column producing the light pulse, the scintillator rod intercepting the radiation can be inferred. In a second variation, illustrated in FIG. 2c, light from several rows or columns of scintillator rods 190 is collected by wave-length shifting optical fibres 40 and transmitted to a position sensitive photodiode or multi-anode photomultiplier 42. By indexing the row and column producing the light pulse, the scintillator rod intercepting the radiation can be inferred.

Since respective photodiodes 21 have no internal gain, the signal conditioning electronics 23 include preamplifiers used in conjunction with high-gain amplifiers in order to amplify the output signal for both neutrons and gamma-rays.

With reference to FIG. 1a, a computer 15 is provided to generate output representing the mass distribution and composition of the object interposed between the sources 12, 14 and detector array 18. A display screen 25 is further provided for displaying images based on the mass distribution and the composition of the ULD 28 being scanned.

The equipment 10 accommodates a ULD 28 with a width up to 2.5 m and a height of 1.7 m. Each ULD 28 to be imaged is mounted on a platform 30 that has runners to engage with a pair of tracks 32. In practice in an airport the ULDs could be scanned while still mounted on their respective dollies that are used to transport the ULDs around the airport. The ULDs and their dollies could be driven onto a platform that would traverse the radiation beams at a known speed. This would minimise the handling of ULDs at the airport.

A further shield in the form of a tunnel 34 is provided. The tunnel 34 is sufficiently long enough so that the equipment can be operated without doors on either end. This permits the number of ULDs passing through the equipment 10 to be maximised.

Figure 1B:
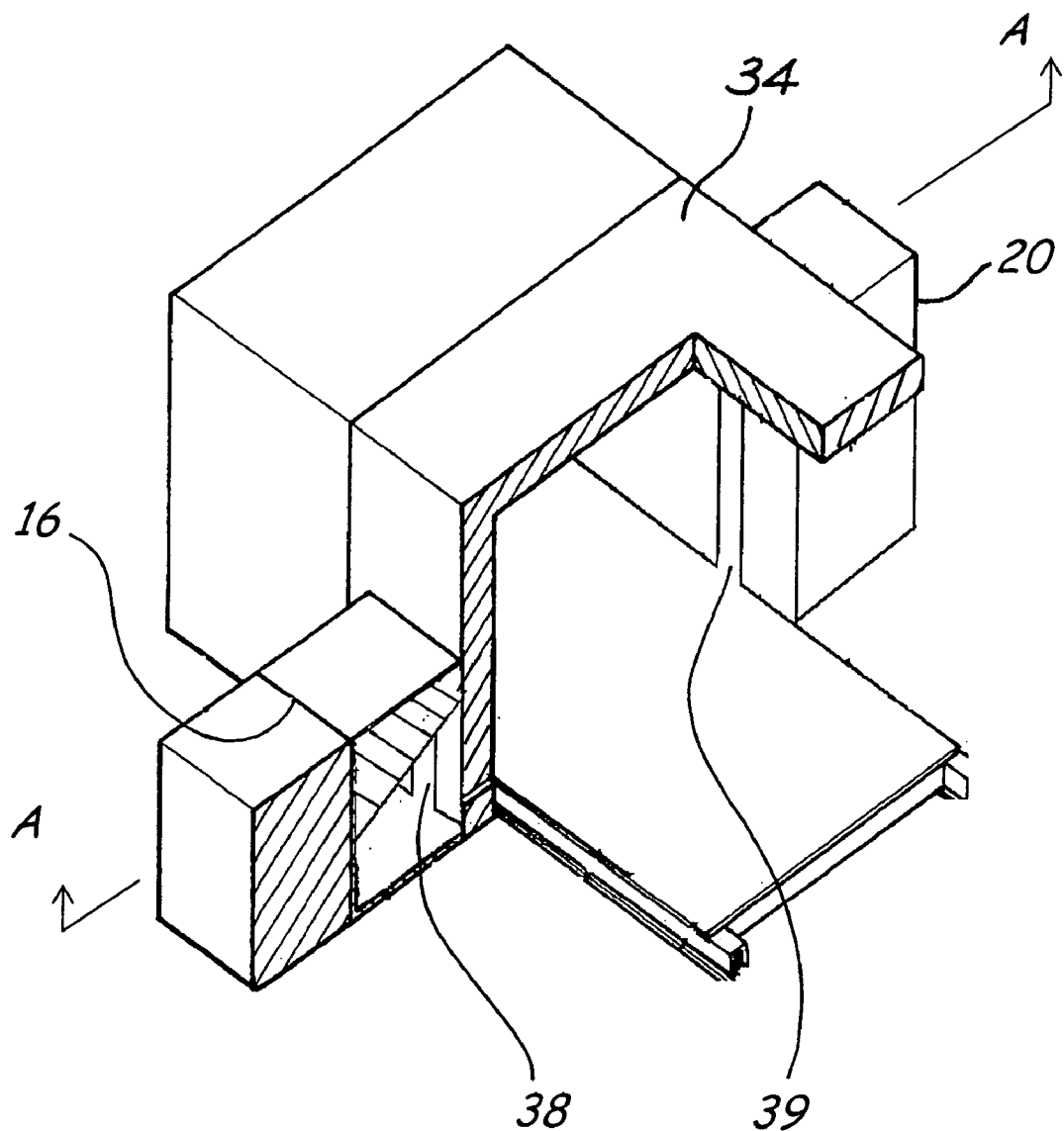
Figure 1C:
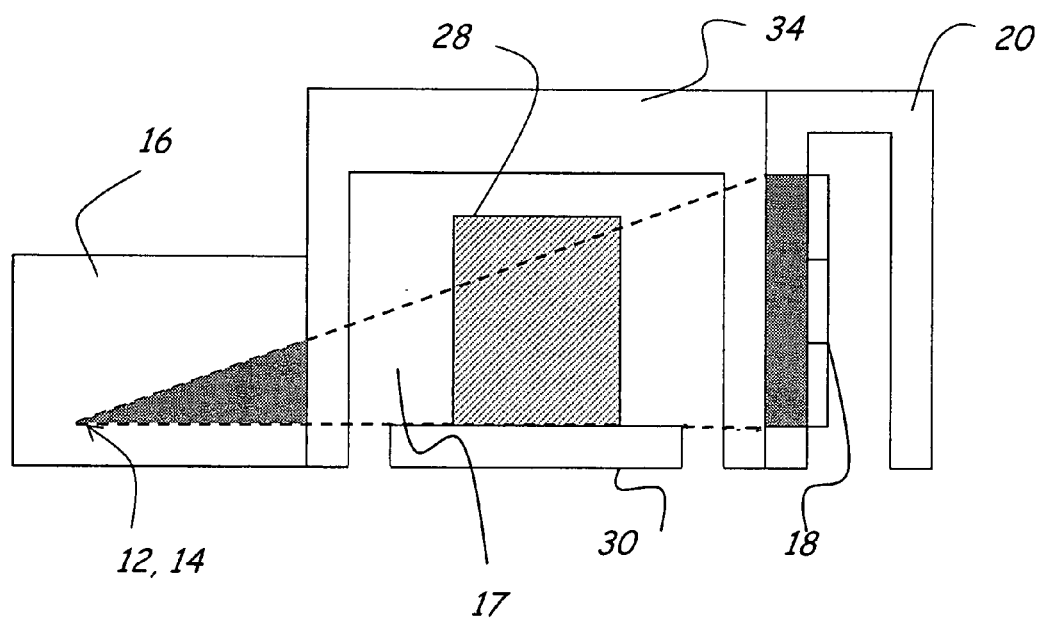
FIG. 1c is a sectional view along line A-A of FIG. 1b.

With reference to FIGS. 1b and 1c, collimating slits 38, 39 are cut into the source and detector shield respectively 16, 20, serve to define a fan shaped radiation beam 17, directed from the sources 12 and 14 towards the radiation detector 18. The detector collimating slit 39 and detector 18 extend the full height of the tunnel 34. Slots (not shown) in the sides of the shield 34 are provided and mate with collimating slits and for the passage of radiation from the sources 12, 14 to the detector 18.

Each of the radiation shields 16, 20 and 34, attenuate and absorb both gamma rays and neutrons. Shielding materials used include concrete, iron and polyethylene. The radiation shields 16, 20 and 34 provide radiological protection for operators of the equipment or other persons in its immediate vicinity.

In operation, objects that are to be imaged are situated on the platform 30 that is then motorised through the tunnel 34. In the full-scale prototype scanner described here the platform 30 is typically operated at a speed such that each 10 mm increment takes approximately forty seconds to collect. This corresponds to a speed of 0.25 mm/sec; consequently, about 2½ hours are required to collect the image of a full ULD. In practice, the speed at which the ULD travels through the equipment can be increased by a factor of over one hundred by increasing the intensity of the neutron source and by increasing the area of the detector array.

As the object passes through the tunnel 34, a scintillation spectrum is collected separately for each element of the 80-pixel array. These spectra are read out and reset every time the platform 30 traverses 10 mm and the spectra are used to deduce neutron and gamma-ray count rates for each pixel. The information in each vertical strip is then assembled to form complete, 2-dimensional neutron and gamma-ray images.

The resulting image has a vertical resolution of 20 mm, governed by the pixel size, and a horizontal resolution of 10 mm, governed by the frequency with which the 80-pixel array is read out. As discussed below, deconvolution of the final image is performed to correct any blurring that may arise as a result of the combination of the motion of the platform 30 during the scan and the 20 mm width of the pixels.

Suppose that the neutron intensity and gamma-ray intensity transmitted though an object and detected in a particular pixel from each image are $I_n$ and $I_g$ respectively and that the neutron intensity and gamma-ray intensity transmitted and detected in a particular pixel from each image without an object present are $I_{on}$ and $I_{og}$ respectively.

Then the attenuation of essentially monoenergetic fast neutrons through an object of density ρ and thickness x can be calculated using the equation:

$$I_n/I_{on} = \exp(-\mu_{14}\rho x) \quad (1)$$

Similarly the attenuation of essentially monoenergetic gamma ray attenuation through the object can be written as:

$$I_g/I_{og} = \exp(-\mu_g \rho x) \quad (2)$$

where $\mu_{14}$ is the neutron mass attenuation coefficient at 14 MeV and $\mu_g$ is the gamma mass attenuation coefficient. The mass attenuation coefficient ratio can then be calculated directly:

$$R = \mu_{14}/\mu_g = \ln(I_n/I_{on})/\ln(I_g/I_{og}) \quad (3)$$

Where R is directly related to the composition of the object and allows a wide variety of inorganic and organic materials and elements to be distinguished.

Figure 3:
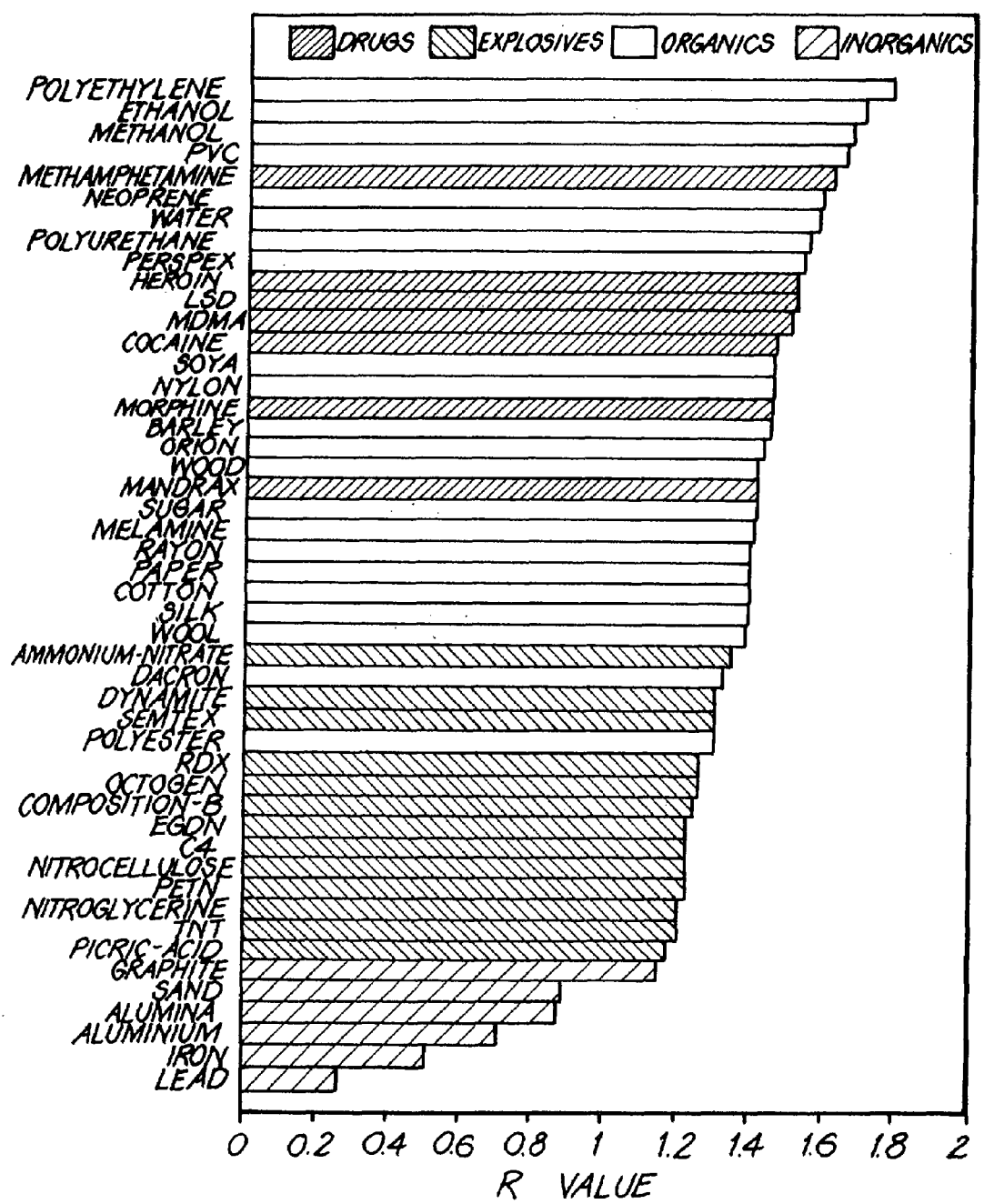
FIG. 3 is a bar graph of the calculated ratio, R, the ratio of the 14 MeV neutron to $^{60}$Co gamma-ray mass attenuation coefficients for a large number of benign, narcotic and explosive materials.
Figure 4:
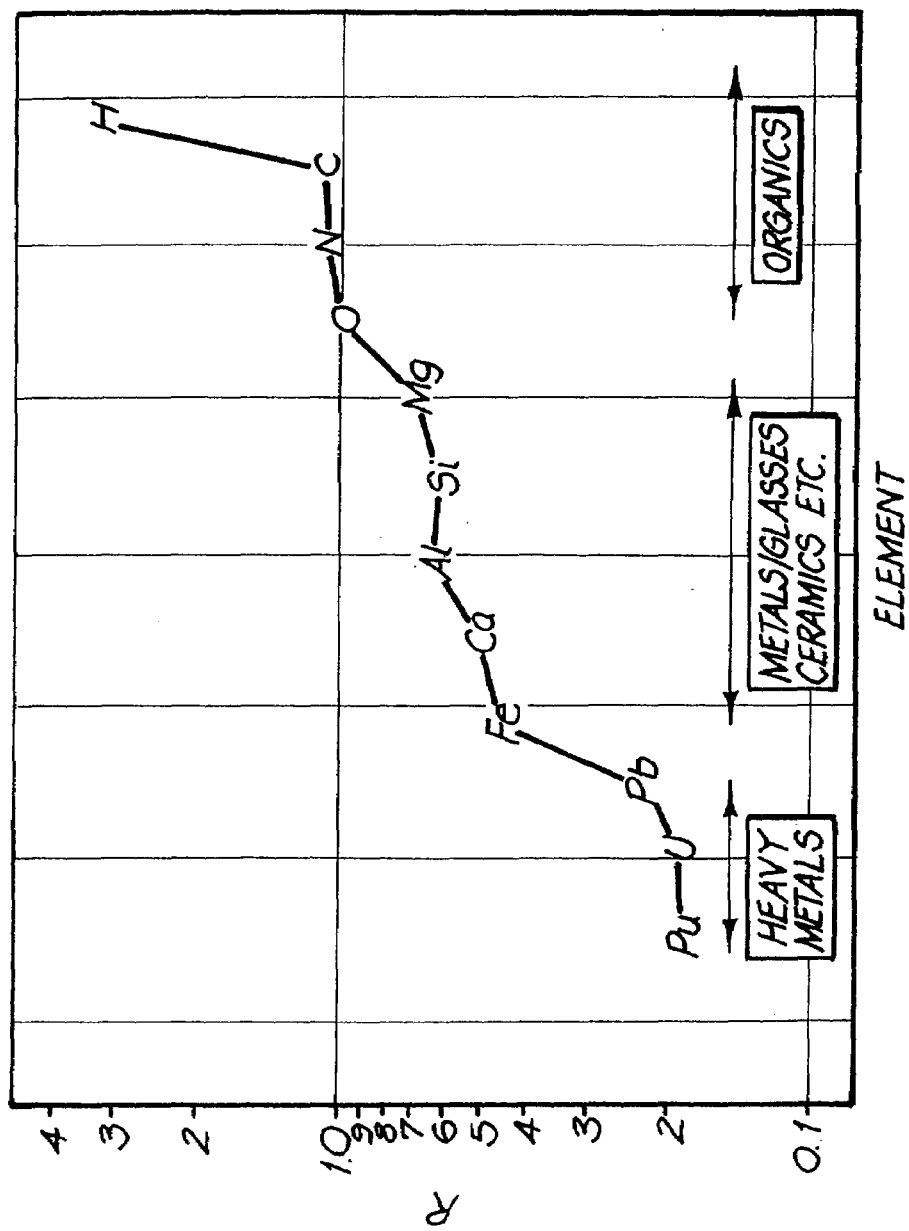
FIG. 4 is a plot of the calculated ratio, R, the ratio of the 14 MeV neutron to the $^{60}$Co gamma-ray mass attenuation coefficients for a range of elements.

FIGS. 3 and 4 illustrate the ability of R to distinguish a wide variety of inorganic and organic materials. Natural materials that are primarily carbohydrate based such as cotton, paper, wood as well as many foods, protein based natural materials such as wool, silk and leather and synthetic organic materials—mainly polymers can be broadly distinguished. As illustrated, inorganic materials such as pottery, ceramics and metal items are easily distinguished from organic materials.

Due to the higher count-rates and lower background scattering of the gamma rays, the gamma-ray image carries most of the information about shape and density. For each pixel in the image, the quantity $\ln(I_g/I_{og})$ is calculated, which is proportional to the total mass per unit area of material along the line from the radiation source to the pixel in question. A "Mexican-hat" sharpening filter is applied to this image to improve object definition and reduce the effects of the motion and pixel-size blurring that affects the horizontal resolution of the image.

The pixel-by-pixel ratio of the neutron and gamma-ray images carries information about the average composition of each pixel, which is independent of the amount of intervening material.

Due to the relatively low counting statistics in the neutron image, there is considerable pixel-to-pixel noise present in the composition image. Consequently, a 5×5-pixel Gaussian smoothing filter is applied to this image. Whilst this reduces the resolution of the composition information in the final image, it significantly enhances the visibility of subtle changes in composition for objects with dimensions of more than about 50 mm.

The results from six scans are shown in FIGS. 5 to 10. The gray-scale images illustrate the results of the gamma-ray scan alone and as such show the results that would be achievable from a conventional X-ray scanner. Regions with little or no intervening material show as white and denser materials show as darker shades of grey. The colour images combine the gamma-ray shape and density information, together with the composition information from the neutron/gamma ratio image. The density of colour shows the material density with white corresponding to no intervening material and denser regions having a saturated colour. The colour of a pixel corresponds to the R value for that pixel, with lower R values coloured blue, intermediate values turquoise through green to yellow and higher values orange. The exact mapping between R value and colour is different for each image, with the colour scale adjusted to show the maximum information in each case. For the ULD scans, an enhanced organic image is also presented. This emphasises organic regions of the image, which are coloured yellow, orange and red.

Figure 5A:
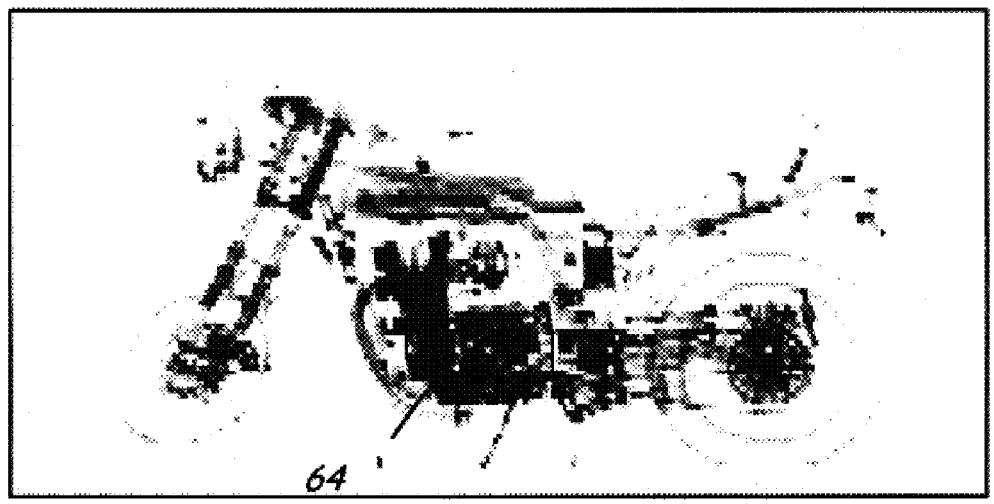
FIG. 5a is a display output of a gamma-ray scan of a motor bike.
Figure 5B:
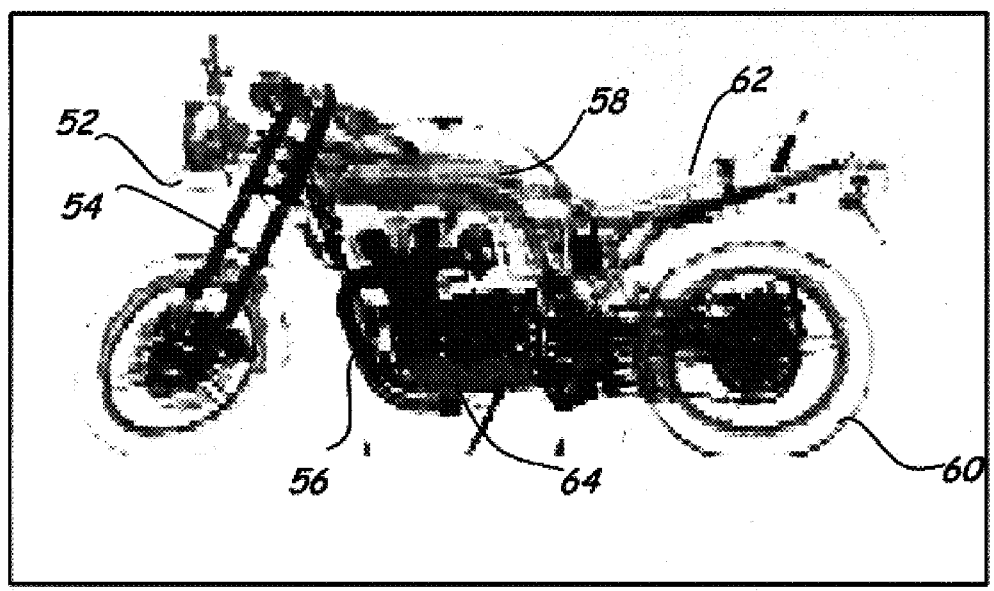
FIG. 5b is a display output in which the image is coloured according to the mass attenuation coefficient ratio, R, for 14 MeV neutrons and gamma rays.

FIG. 5*a* illustrates the result of the gamma ray scan alone of a motorbike. FIG. 5*b* illustrates the combined gamma-ray shape and density information together with the composition information from the neutron/gamma ratio image scan of a motorbike. This image provides a good indication of the overall imaging capabilities of the equipment. In particular, fine details such as the front brake cables 52 show quite clearly in FIG. 5*b*, even though they are considerably smaller than the 20 mm pixel size. The metal frame 54 and engine 56 of the bike show up blue in figure 5*b*; whereas the fuel 58 in the petrol tank, rubber tyres 60, plastic seat 62 and plastic lights show up orange. The oil 64 in the sump (immediately above the kickstand), when averaged together with the metal around it shows as a green patch. In contrast, from the conventional gamma-ray image FIG. 5*a*, it is difficult or impossible to distinguish between the oil 64 and the sump.

Figure 6A:
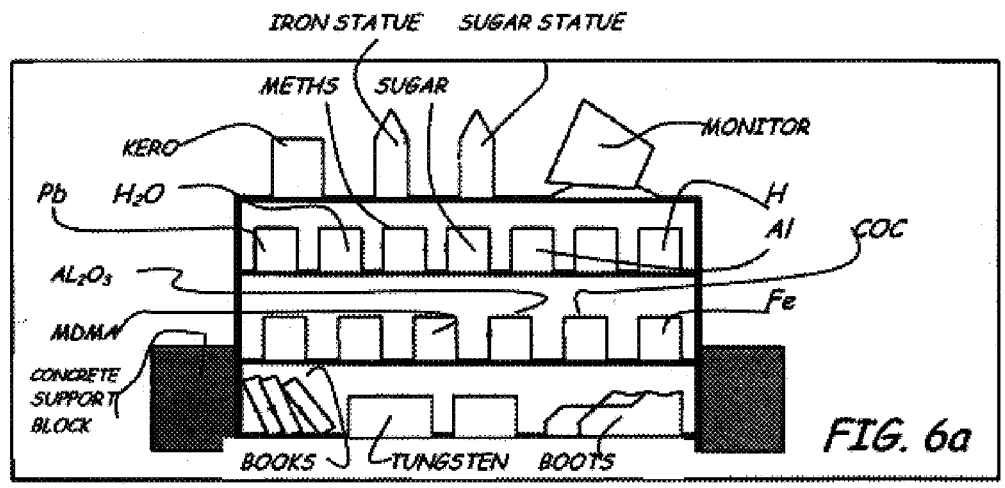
FIG. 6a is a schematic illustration of a selection of material samples and common objects arranged on wooden shelves.
Figure 6B:
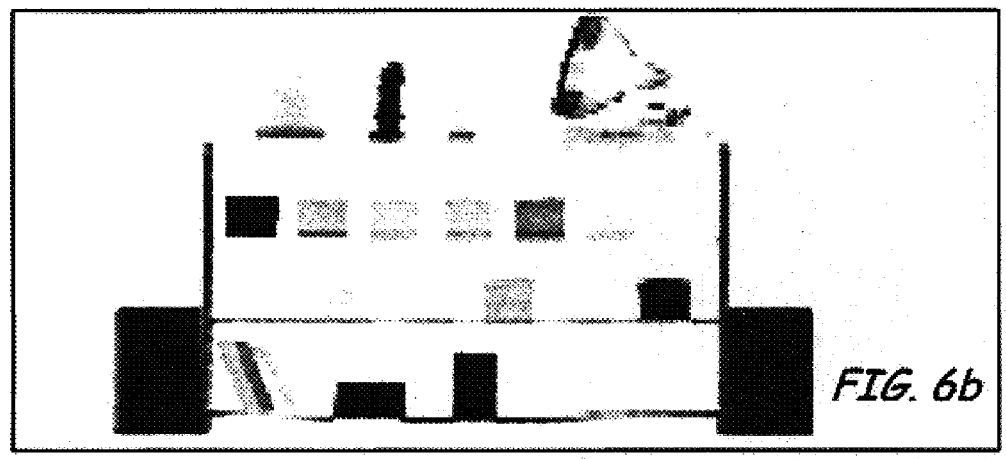
FIG. 6b is a display output of a gamma-ray scan.
Figure 6C:
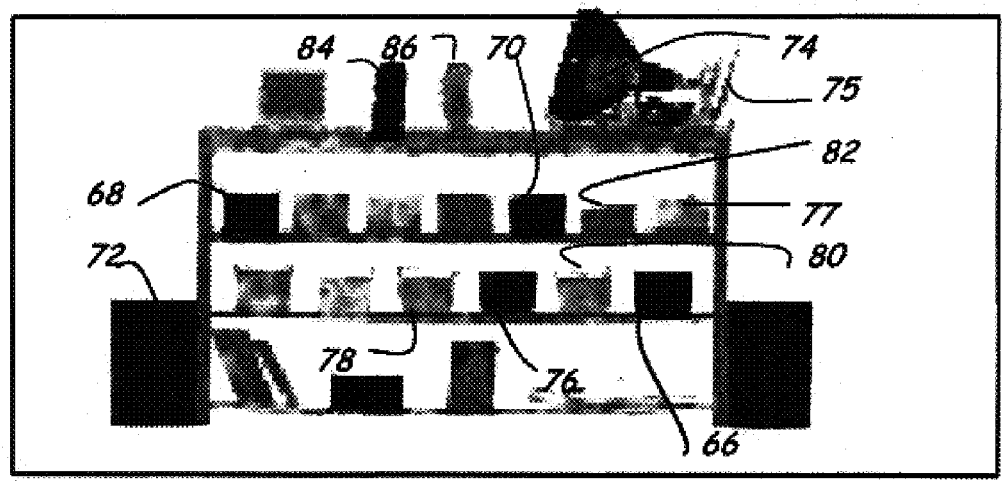
FIG. 6c is a display output in which the image is coloured according to the mass attenuation coefficient ratio, R, for 14 MeV neutrons and gamma rays.

FIGS. 6*a* to 6*c* illustrate a selection of material samples and common objects arranged on wooden shelves. Again, as illustrated in FIG. 6*c*, metals such as iron 66, lead 68 and aluminium 70 show up dark-blue. Intermediate materials such as concrete 72, glass 74 (in the computer monitor 75) and ceramic powder (alumina, $Al_2O_3$) 76 show up lighter blue. Finally, the organic materials, including elemental simulants of heroin 77, methamphetamine 78, cocaine 80 and TNT 82 show up in a variety of colours from green to orange, depending on the R value of the material. Two ceramic statues on the top shelf, one filled with iron shot 84 and the other with sugar 86 can be clearly distinguished, both by density and by composition.

Figure 7A:
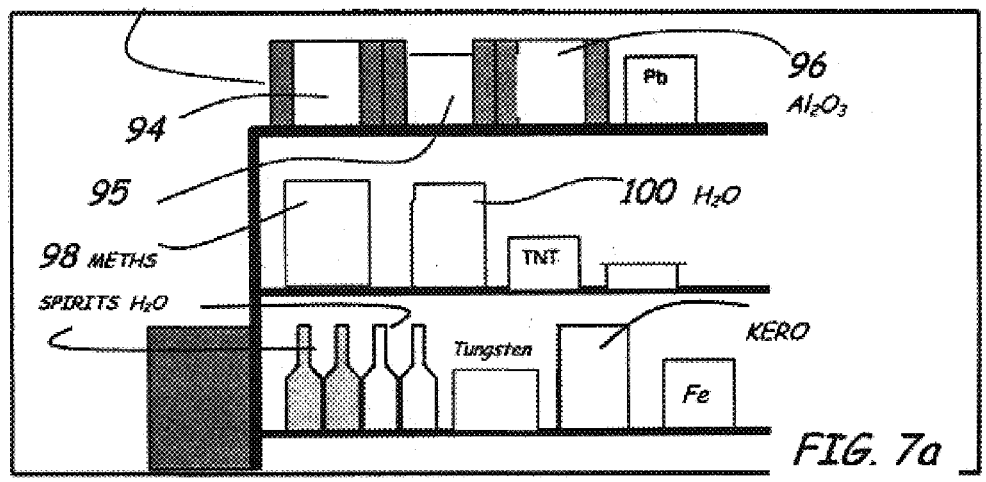
FIG. 7a is a schematic illustration of a selection of material samples, concealed contraband, alcohol, as well as simulated and real explosives.
Figure 7B:
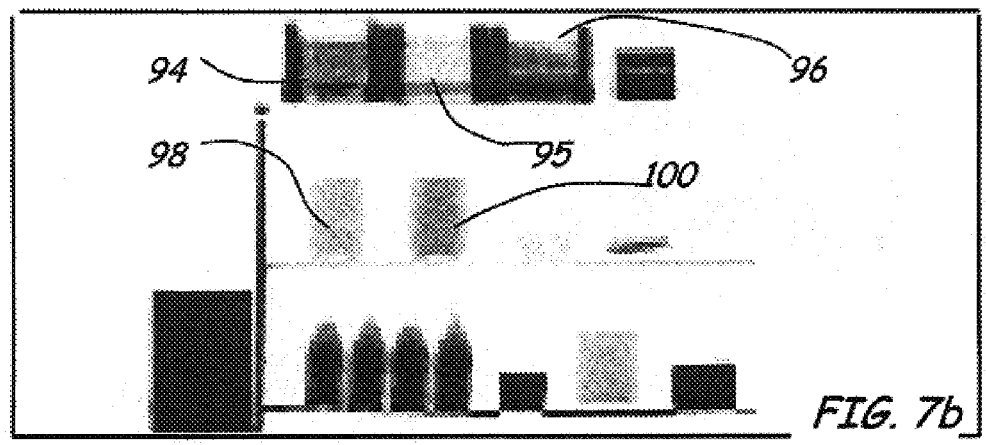
FIG. 7b is a display output of a gamma-ray scan.
Figure 7C:
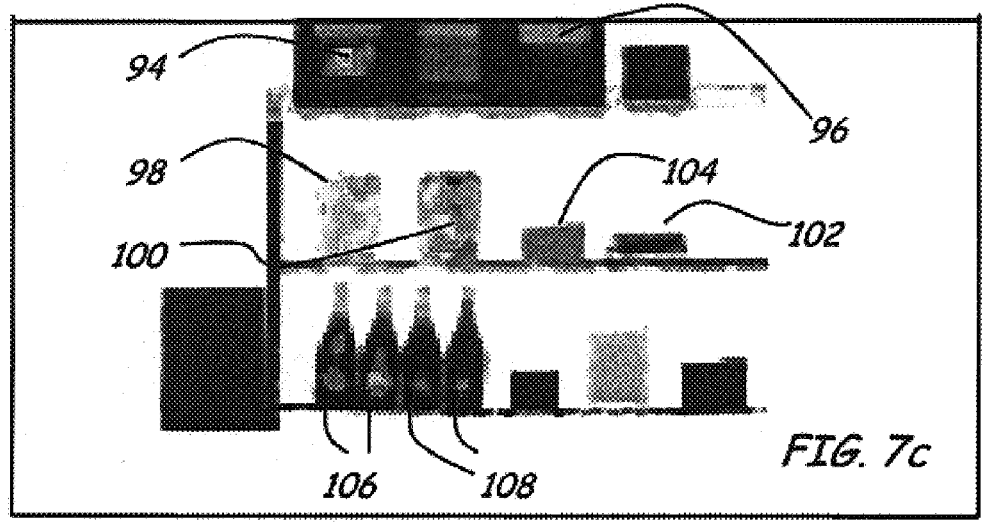
FIG. 7c is a display output in which the image is coloured according to the mass attenuation coefficient ratio, R, for 14 MeV neutrons and gamma rays.

FIG. 7*a* to 7*c* illustrate a further selection of materials, including concealed contraband, alcohol and both simulated and real (Detasheet) explosives. Three hollow concrete blocks are positioned on the top shelf. The left-hand block contains concealed organic material 94 (drug substitute); the centre block is empty and the right hand block contains alumina powder 96. These three blocks provide simple models of drugs concealed within a ceramic or pottery object, a hollow, empty object and a hollow, empty object with thickened walls. Whilst the gamma-ray image of FIG. 7*b* clearly distinguishes between the empty 95 and filled blocks 94 and 96, it cannot separate the drug-surrogate filled block 94 from the alumina filled block 96. In contrast, the neutron image of FIG. 6*c* clearly reveals the concealed organic filling 94 shown as a yellow/orange patch. On the left hand side of the middle shelf are positioned two containers, one filled with pure alcohol 98 (Meths) and one with water 100 ($H_2O$). The alcohol 98 shows clearly as being more 'organic' (higher R value) and is predominantly orange in colour; the water 100, with a lower R value is predominantly green. On the same shelf, the simulated 102 and real 104 explosives show as the same colour showing that the simulant is a good substitute for real explosive. On the bottom shelf is a case containing twelve glass bottles of which only four are visible, two filled with simulated spirits 106 (40% ethanol, 60% water) and two filled with water 108. Again, the alcohol filled bottles 106 show up as having a higher R value (more green/orange) than the water 108 (predominantly blue). This is in contrast to the bottles shown in FIG. 7*b* which are almost indistinguishable.

FIGS. 8*a* to 8*d*, 9*a* to 9*d* and 10*a* to 10*d* illustrate the results of imaging ULDs filled with a variety of objects. In all three figures, the filling of the ULD has been deliberately kept fairly simple, to simplify discussion of the results obtained. In particular, most of the packing material that would normally be present (cardboard boxes, foam, polystyrene etc) has been omitted so that the objects in the ULD can be clearly seen. It is recognised that in reality, most ULDs would be considerably more cluttered.

Figure 8A:
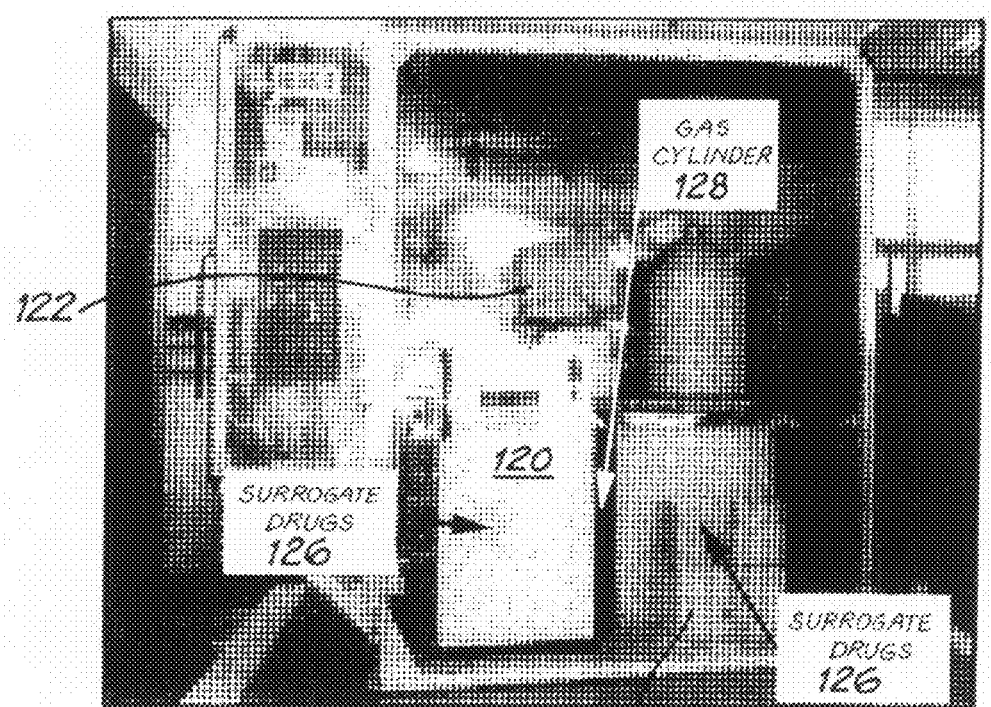
FIG. 8a is a photograph of a ULD containing assorted household electronics metal items, concrete blocks and concealed contraband.
Figure 8B:
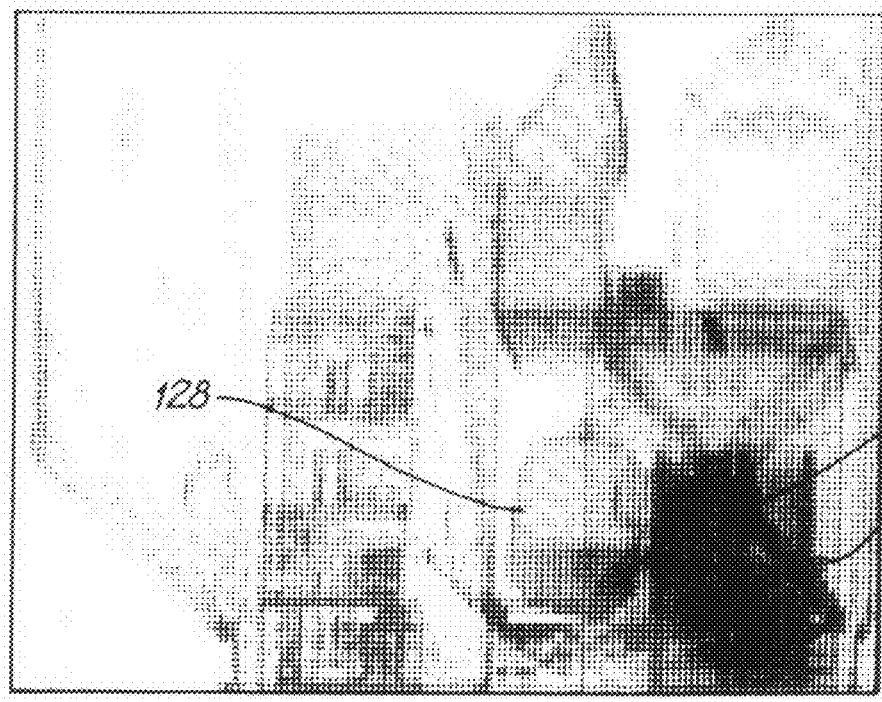
FIG. 8b is a display output of a gamma-ray scan.
Figure 8C:
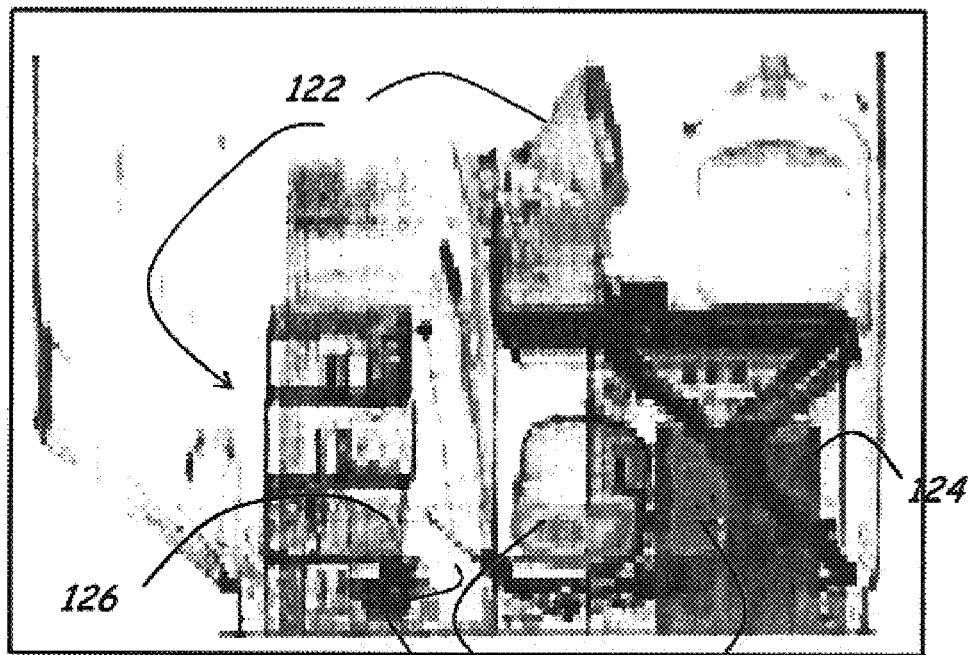
FIG. 8c is a display output in which the image is coloured according to the mass attenuation coefficient ratio, R, for 14 MeV neutrons and gamma rays.
Figure 8D:
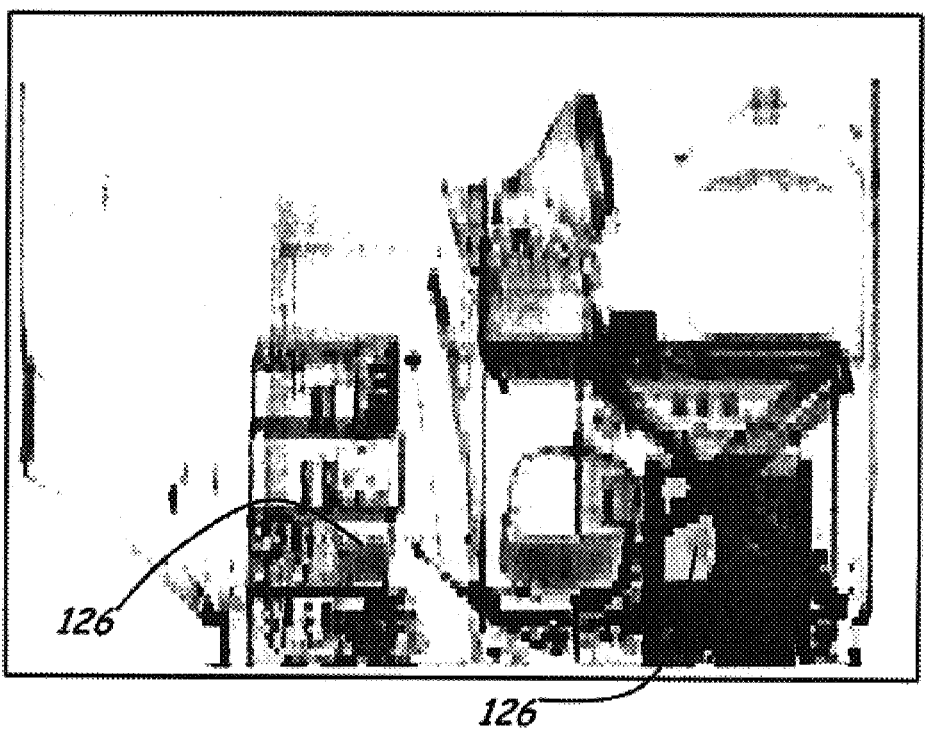
FIG. 8d is the display output of figure 8c which has been further processed to emphasise the organic material.
Figure 9A:
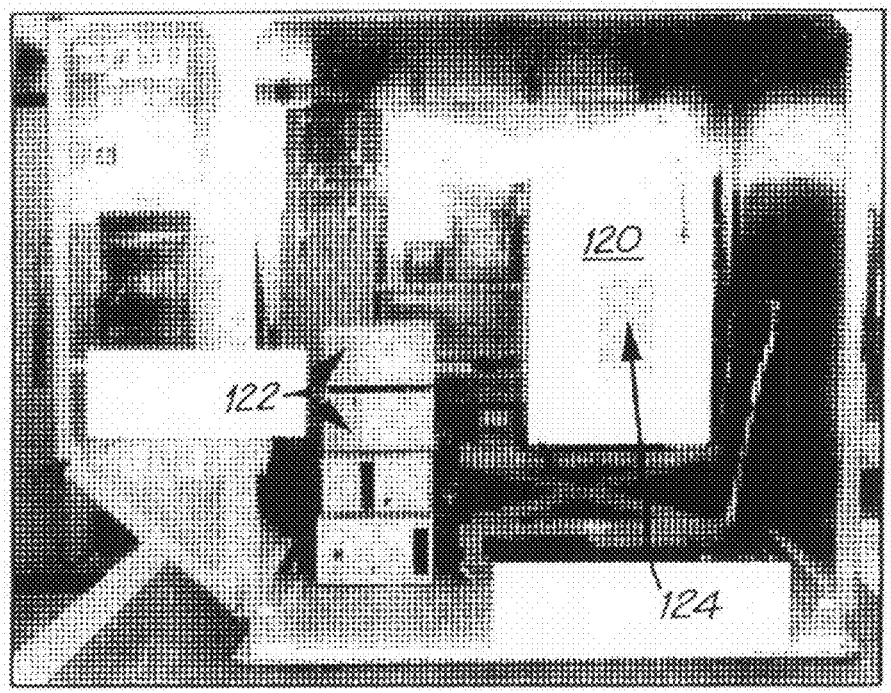
FIG. 9a is a photograph of a ULD containing assorted household items and concealed drugs.
Figure 9B:
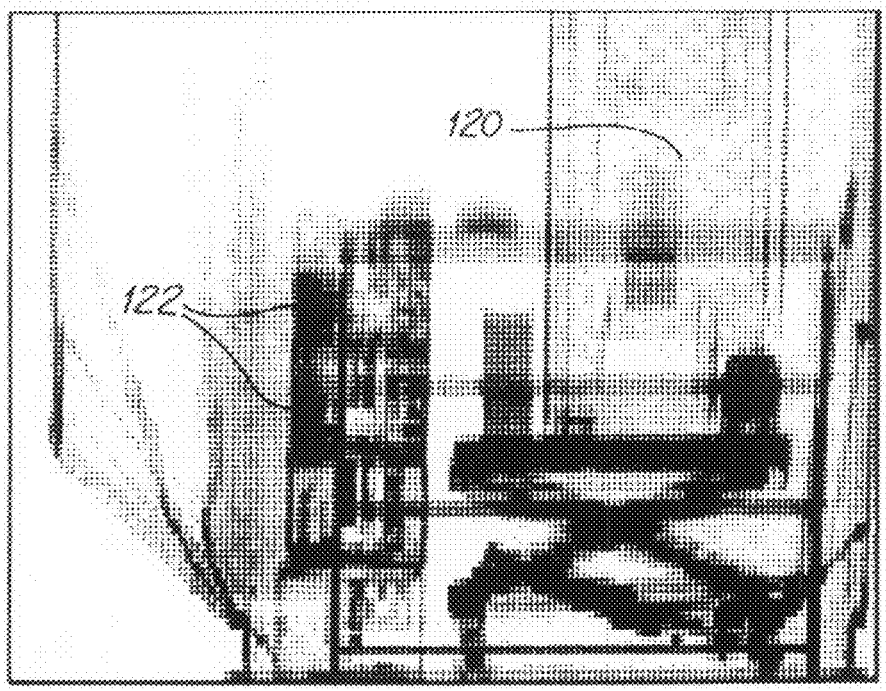
FIG. 9b is a display output of a gamma-ray scan.
Figure 9C:
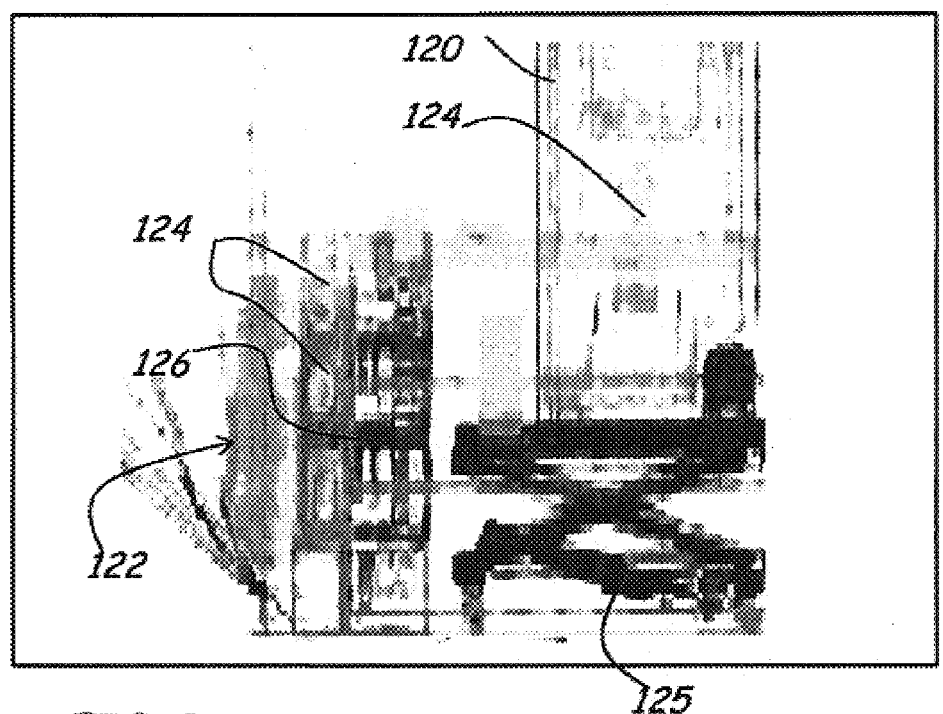
FIG. 9c is a display output in which the image is coloured according to the mass attenuation coefficient ratio, R, for 14 MeV neutrons and gamma rays R.
Figure 9D:
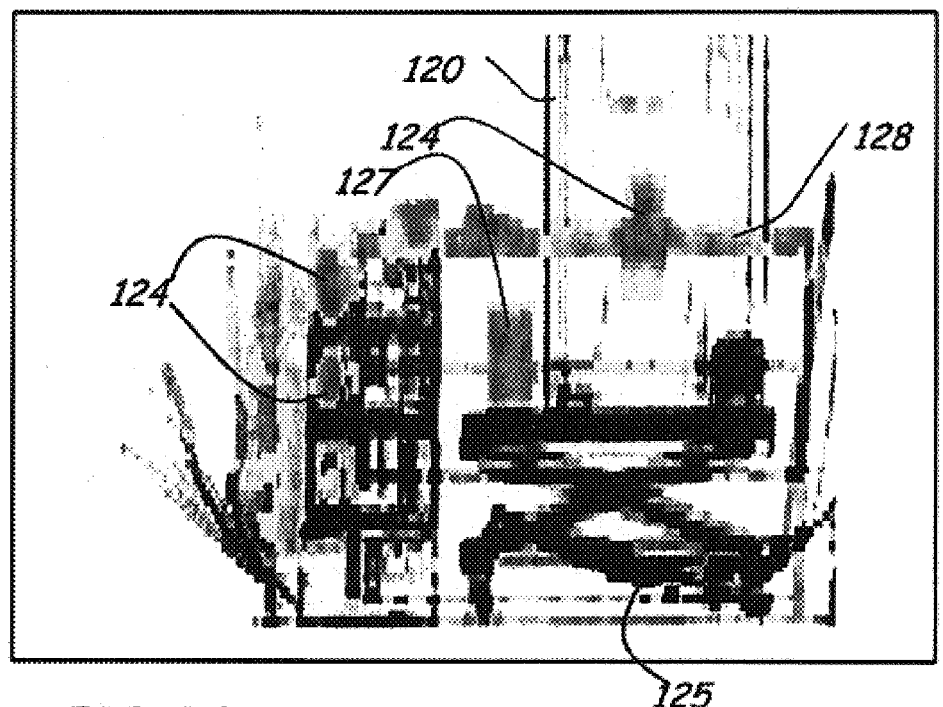
FIG. 9d is the display output of FIG. 9c which has been further processed to emphasise the organic material.
Figure 10A:
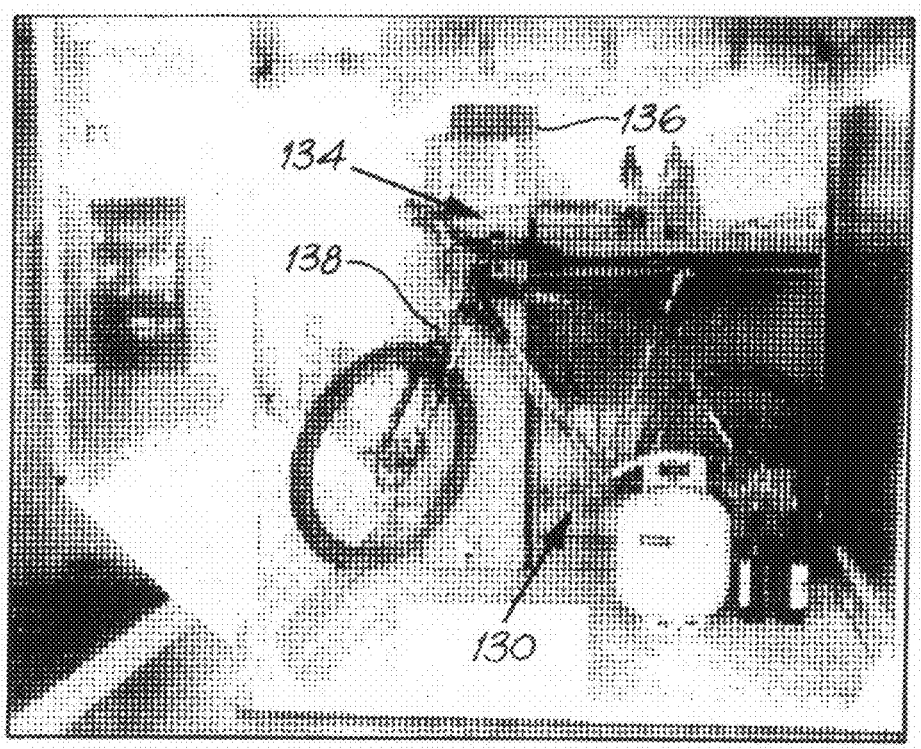
FIG. 10a is a photograph of a ULD containing assorted household items and concealed drugs.
Figure 10B:
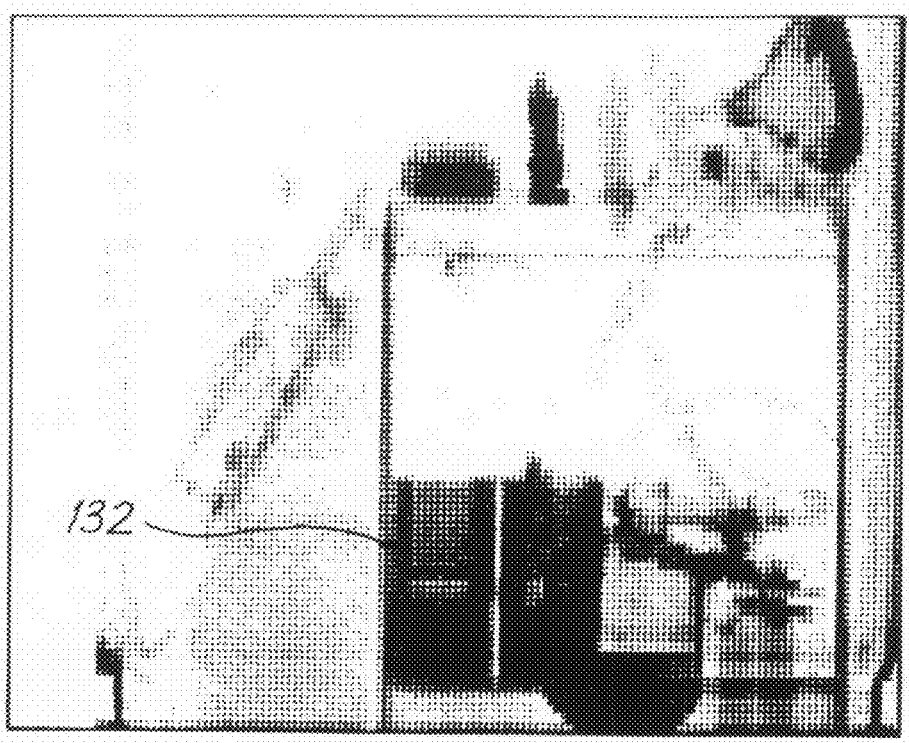
FIG. 10b is a display output of a gamma-ray scan.
Figure 10C:
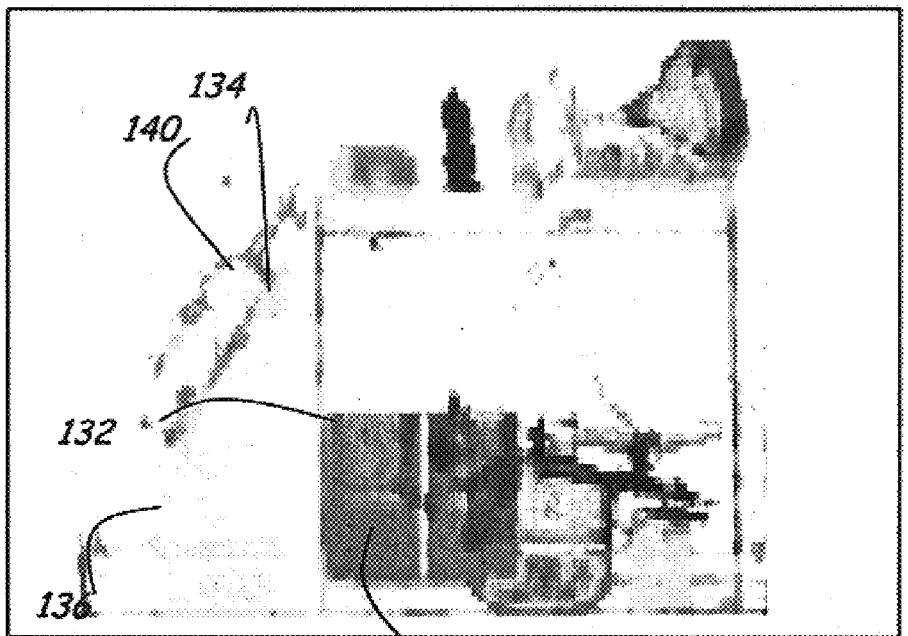
FIG. 10c is a display output in which the image is coloured according to the mass attenuation coefficient ratio, R, for 14 MeV neutrons and gamma rays.
Figure 10D:
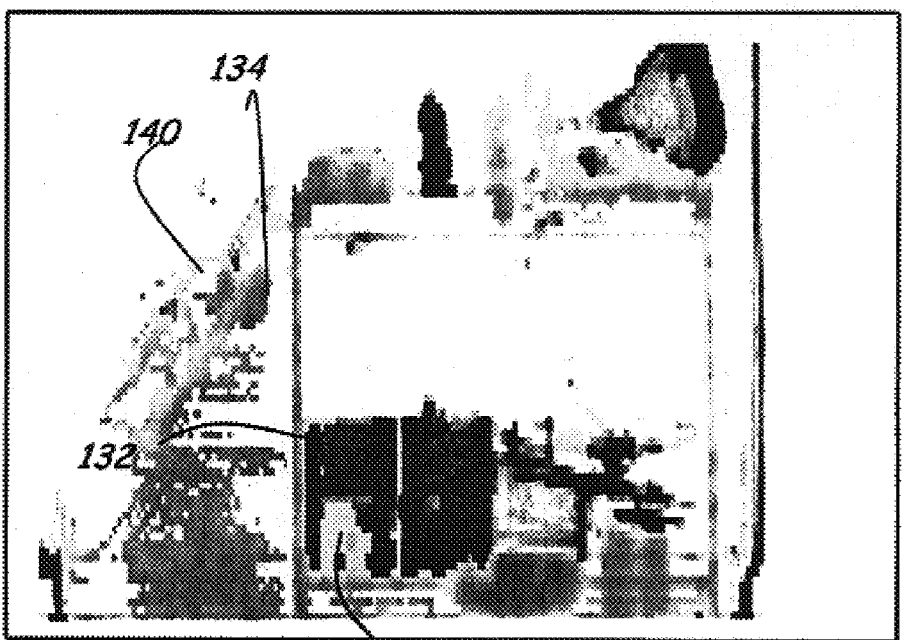
FIG. 10d is the display output of figure 10c which has been further processed to emphasise the organic material.

FIGS. 8*a* to 8*d* illustrates a ULD filled with a variety of household electronics (a refrigerator 120 and several computers 122), metal parts, hollow concrete blocks 124 (substituting for ceramic pipes or hollow statues or figurines) and tools. Two packets of plastic beads, substituting for drugs 126, are concealed within one of the computers and inside one of the concrete blocks. A propane gas cylinder 128 is also hidden inside the ULD. FIG. 8*a* illustrates a photograph of the ULD scanner. FIG. 8*b* shows the results of the gamma-ray scan only. Neither of the packets of surrogate drugs 126 are particularly obvious. The propane gas cylinder 128 can be identified on the basis of its shape, although the organic nature of its contents is not clear. FIGS. 8*c* and 8*d* are coloured according to the neutron/gamma ratio R, as a result the inorganic materials show up in FIG. 8*c* as blue (the computer 122 and blocks 124) and the organic materials as orange (the surrogate drugs 126 and the gas cylinder 128). The proportions in which the two images are combined are adjusted by the operator to maximise contrast and sensitivity for organic materials which are coloured yellow and red and to minimise the effects of clutter resulting from overlapping objects, the result is illustrate in FIG. 8d. Clearly both packets of concealed drugs 126 can be identified.

FIGS. 9a to 9d illustrates a ULD with drugs 124 concealed inside two computers 122 and a fridge 120. Whilst it can be seen in the gamma-ray image of FIG. 8b that the top two computers 122 appear somewhat different from the bottom two, it is not clear whether this is a genuine difference in the structure of the machines. However, in the FIGS. of 9c and 9d it is immediately apparent that the difference is due to a large volume of organic material, as shown by the bright orange colour of these regions with drugs 124. The top two computers 122 contain ~1 kg bags of plastic beads simulating packaged drugs. This is in contrast to the predominantly blue (inorganic or low R value) colour of the rest of the computer structure 126. Similarly, it is not clear from the gamma-ray image of FIG. 9b of the fridge 120 whether the anomaly in the centre of the image is part of the structure of the fridge or not. However, in FIGS. 9c and 9d it can be seen that the anomaly 124 is clearly organic and in contrast to the predominantly inorganic structure visible in the rest of the fridge (in particular, the compressor 125 at the lower right and the freezer compartment at the top). Again, in the enhanced organic image of FIG. 9d the concealed drugs 124 are clearly visible. Additionally, other organic material in the ULD (notably the wooden shelving 128 behind the fridge 120 and the container of water 127 to the left of the fridge 120) also shows up as orange.

FIGS. 10a to 10d illustrate a second ULD with real concealed drugs (1 kg each of heroin and methamphetamine). The heroin 130 is hidden inside a hollow concrete block 132. The methamphetamine 134 is hidden inside a small box, which is placed inside a larger box 136 filled with clothing. The organic nature of the concealed drugs is evident from the colouring in the composition images of FIGS. 10c and 10d. Once again, the enhanced organic image of FIG. 10d effectively reveals the concealed drugs 130 and 134, especially the heroin 130 coloured yellow inside the concrete blocks 132. As the methamphetamine 134 is concealed within the box 136 of clothing (immediately behind the front fork of the bicycle 140), composition discrimination is less revealing in this case. However, the package of drugs 134 can be identified as a potential anomaly on the basis of its shape and higher density.

The radiographic equipment as described can be used in at least three ways for detecting and identifying contraband materials. Firstly, the gamma-ray images provide considerable information about the shapes, sizes and densities of objects inside an object such as a ULD. Some suspicious materials can be identified on this basis. Particular examples would be packets of drugs concealed inside spaces or cavities of hollow objects. Secondly, the colouring of the gamma-ray image on the basis of composition information derived from the neutron measurements provides powerful extra clues in the interpretation of scan images and identification of suspicious materials. In particular, the detection of organic materials inside predominantly inorganic objects is greatly facilitated. Thirdly, under certain circumstances, the equipment can be used to measure the neutron/gamma ratio (R values) of suspicious materials to further assist in their identification. This approach works best when there is little over- or under-lying material around the substance being measured, or when the over- and under-lying material is reasonably uniform in the immediate vicinity of the measurement region. Under these circumstances, it is possible to make an approximate correction for the absorption of neutrons and gamma rays in the over- and under-lying material to obtain the R value of just the substance of interest.

A second embodiment applies directly to the dual energy fast neutron transmission embodiment for 14 MeV and 2.45 MeV. However the following discussion also applies to the dual energy transmission at different energies to 2.45 and 14 MeV. However unlike single energy neutron transmission discussed previously, three count rates are measured at each pixel rather than two in the case of single neutron transmission, and two-cross-section ratios can be calculated.

Suppose that the count rates in a particular pixel from each image are $r_{14}$, $r_{2.45}$ and $r_x$ respectively. These rates are related to the (unknown) mass of material m between the source and detection points and the (unknown) mass attenuation coefficients of this material for 14 MeV neutrons, 2.45 MeV neutrons and X- or gamma-rays, written as $\mu_{14}$, $\mu_{2.45}$ and $\mu_X$ respectively, by the relations:

$$r_{14}=R_{14}\exp(-m\mu_{14}) \qquad (4)$$

$$r_X=R_X\exp(-m\mu_X) \qquad (5)$$

$$r_{2.45}=R_{2.45}\exp(-m\mu_{2.45}) \qquad (6)$$

where $R_{14}$, $R_{2.45}$ and $R_X$ are respectively the count rates for 14 MeV neutrons, 2.45 MeV neutrons and X- or gamma-rays when no intervening object is present.

The cross-section ratios can be calculated directly:

$$\mu_{14}/\mu_X=\log(r_{14}/R_{14})\log(r_X/R_X) \qquad (7)$$

$$\mu_{2.45}/\mu_{14}=\log(r_{2.45}/R_{2.45})\log(r_{14}/R_{14}) \qquad (8)$$

Note that both of these ratios are independent of the mass of material present in the beam between the source and detector.

The cross-section ratios given by equations (7) and (8) allow a wide variety of organic and inorganic materials to be distinguished.

Figure 11:
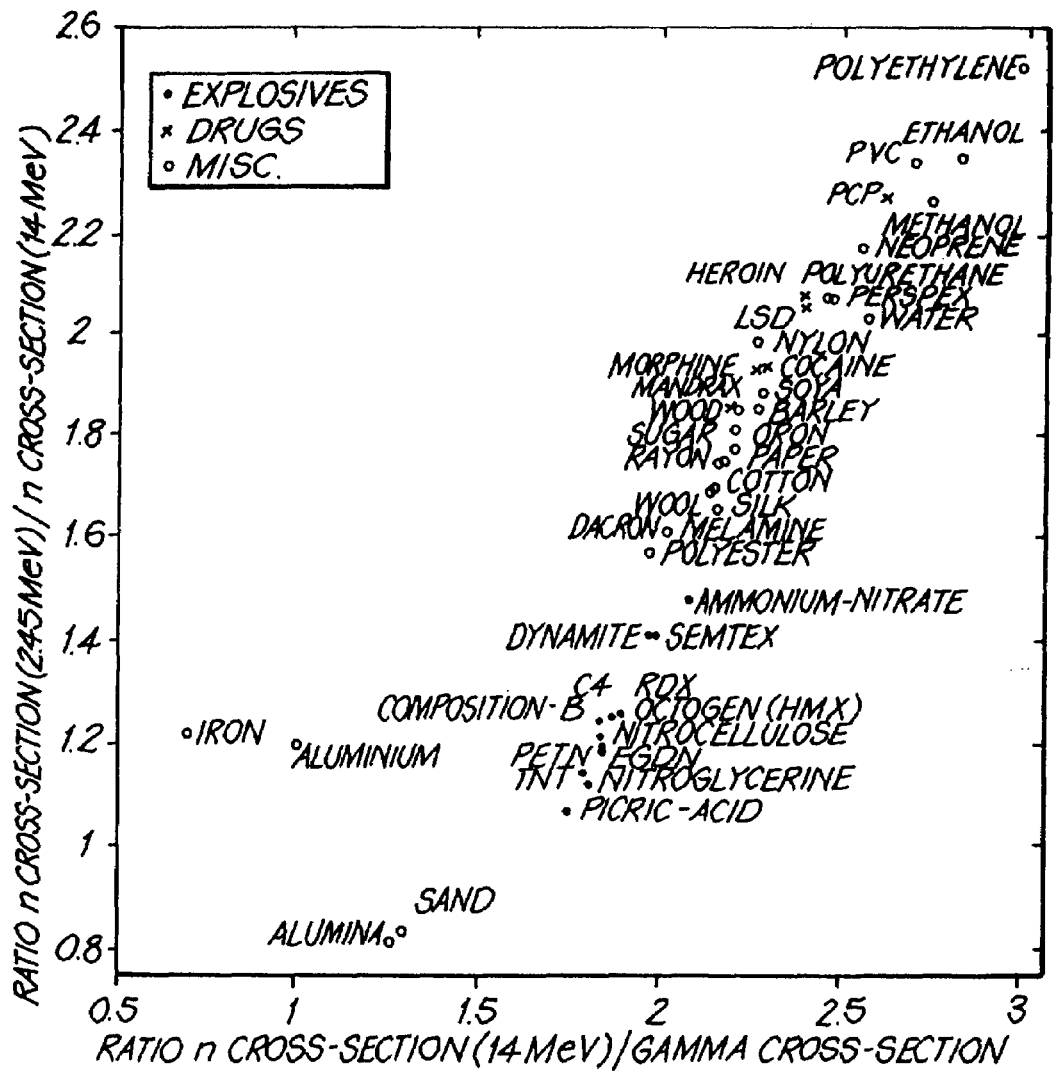
FIG. 11 is a plot of a large number of benign, narcotic and explosive materials in terms of two cross-section ratios, namely 2.45 MeV neutron/14 MeV neutron cross-sections versus 14 MeV neutron/X- or gamma-ray cross-sections.

FIG. 11 illustrates the ratio of 2.45 MeV neutron cross-section to 14 MeV neutron cross-section versus the ratio of 14 MeV neutron cross-section to X- or gamma-ray cross-section, for a selection of materials. The availability of two cross-section ratios further enhances the ability of the invention to distinguish between different materials. Consequently, analysis of the three mass-attenuation coefficient images allows information about the contents of the object being examined to be inferred.

FIG. 12 illustrates the additional benefit of using dual neutron energies, consider the simulated images of a suitcase 150 shown in FIGS. 12a to 12e. Images 12a to 12c correspond to equations (4) (5) and (6) and show the transmission of 14 MeV neutrons, 2.45 MeV neutrons and X- or gamma-rays respectively. Images 12d to 12e correspond to equations (7) and (8) and show the DT/X-ray and DD/DT cross-sections respectively.

The suitcase 150 is filled with clothing composed of cotton and wool, and contains various benign and suspicious objects. Bottle 152 contains water and bottle 154 contains spirits. The three blocks visible on the lower right of the suitcase 150 are a paperback book 156, heroin 158 and RDX explosive 160. A gun 162 is also visible in the upper right of the suitcase 150.

Figures 12A, 12B:
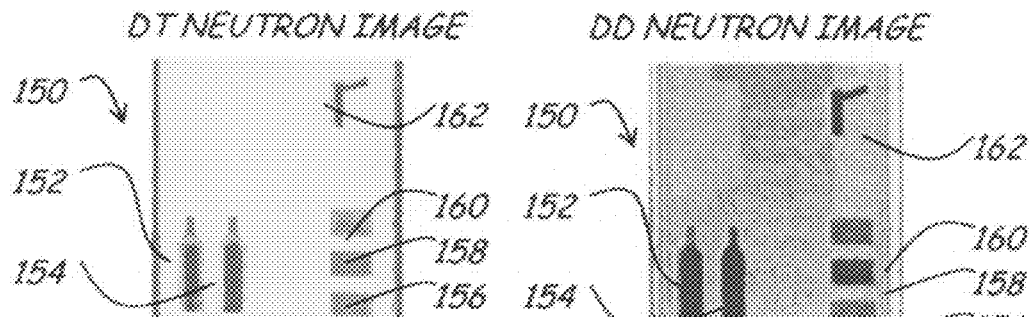
FIG. 12a is a simulated count rate DT neutron image of a suitcase.
FIG. 12b is a simulated count rate image of a DD neutron image of the suitcase.
Figure 12C:
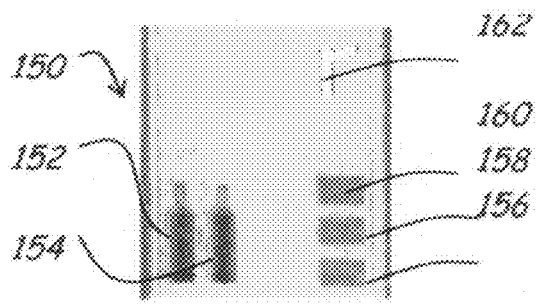
FIG. 12c is a simulated count rate X ray image of the suitcase.
Figure 12D:
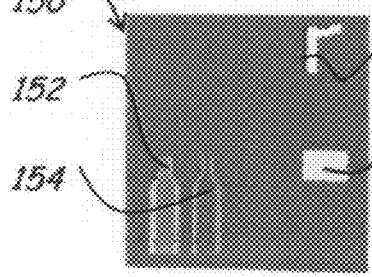
FIG. 12d is a DT/X-ray cross section image and FIG. 12e is a DD/DT cross-section image.
Figure 12E:
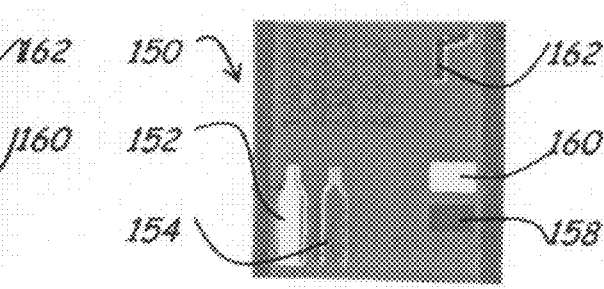

From a conventional X-ray image 12c, it is difficult or impossible to distinguish between the contents of the two bottles 152, 154, or the three packages 156, 158, 160 on the right hand side of the case that have similar densities. The neutron images 12a, 12b provide more contrast between the different materials, but the best results are obtained from the cross-section ratio images 12*d* and 12*e*. In particular, the book 156 as shown in FIGS. 12*a* and 12*b* virtually disappears in FIGS. 12*d* and 12*e* as paper has a similar composition to the surrounding clothing, whereas the drugs 158 in FIG. 12*e* and explosive materials 160 in FIGS. 12*d* and 12*e* can be clearly distinguished. A clear difference is also seen in both FIGS. 12*d* and 12*e* between the bottles containing water 152 and spirits 154.

In a first variation of the dual neutron transmission method, the operator would form a new image that is a linear combination of the two cross-section ratio images. The proportions in which the two images are combined are adjusted by the operator to maximise contrast and sensitivity for contraband materials and to minimise the effects of clutter resulting from overlapping objects.

Figure 13A:
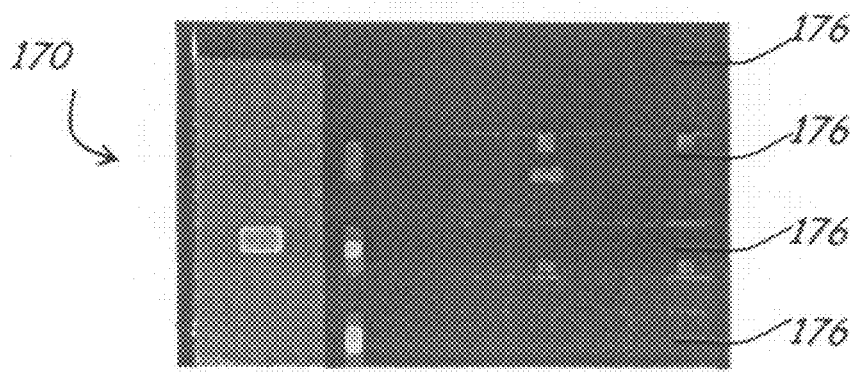
FIG. 13a is a simulated 14 MeV neutron image of an air freight container.
Figure 13B:
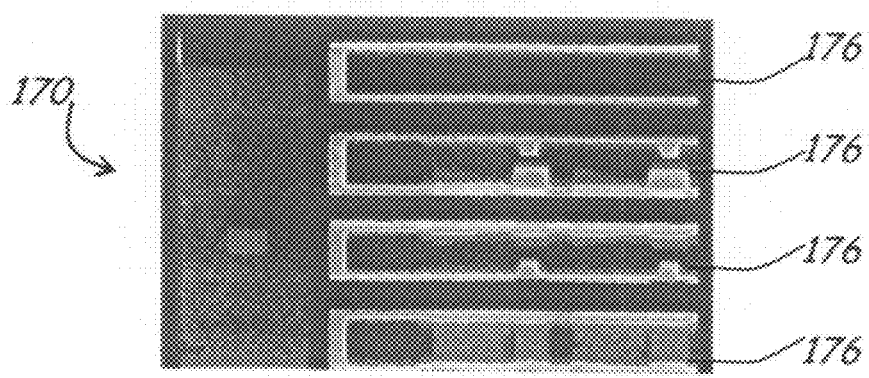
FIG. 13b is an X-ray image respectively of the same container.

FIGS. 13*a* to 13*b* illustrate simulated 14 MeV neutron and X-ray images respectively of a container 170, taken from the side. Due to their high density, the steel pipes 176 dominate the images, making it hard to see the outlines of the computer equipment. However, by forming a single image, FIG. 13*c*, from the two cross-section ratio images given by equations (7) and (8), it is possible to remove the "clutter" associated with the steel pipes 176, to reveal the computer boxes 174.

Figure 13C:
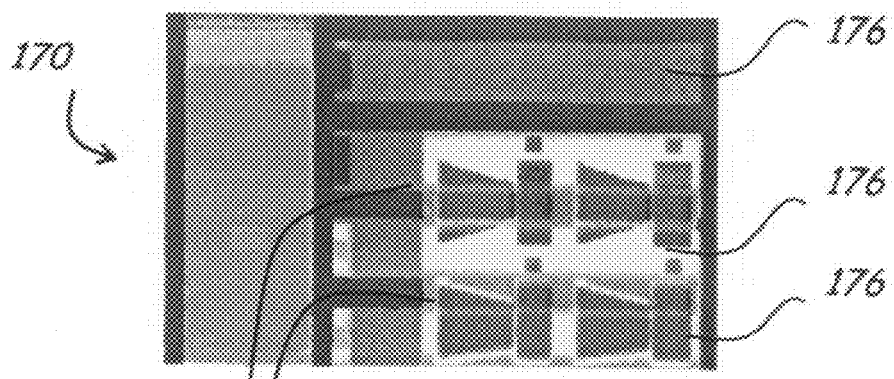
FIG. 13c is a combined image of the same container.

This approach can be understood with reference to FIG. 11. Choosing a linear combination of images (7) and (8) is equivalent to colouring image pixels according to their distance from an arbitrarily orientated line drawn on FIG. 11. By choosing this line to be parallel to two selected materials, any combination of these materials is coloured the same. In the example discussed, the line is chosen to be parallel to a line connecting steel and the polystyrene packaging of the computers. In this way, the steel pipes can be made to largely vanish where they pass in front of the computers. FIG. 13*c* shows the results of this process.

Although one such example of the invention has been discussed, it should be appreciated that such an embodiment is only one of the many utilising the principles of the invention. Whilst in the above example, the radiation sources are situated on one side of the object to be examined and the detectors on the opposite side, in a first variation, the sources are situated above or below the object to be examined, with the detectors positioned on the opposite side (below or above respectively). In a second variation, the sources and detectors can be rotated around the object to be examined to allow multiple views to be obtained. In a third variation, multiple sets of sources and detectors are used to allow simultaneous collection of multiple views of the same object. In a fourth variation, multiple sets of detectors are disposed around a central source to allow views of multiple objects to be acquired simultaneously.

Of course, in operation, objects that are to be scanned may be passed through the tunnel on a conveyor belt or winched or pushed through using a suitable mechanism.

Whilst in the above embodiment, the two radiation sources are operated sequentially as the object is scanned through the analyser. In a first variation, the object is scanned through the analyser twice, with one source being operated for each scan. In a second variation, each source has a separate associated detector and the object is scanned only once. In a third variation, the two radiation sources are operated at the same time, a single detector is used and energy discrimination is used to separate the signals due to neutron and X- or gamma-rays.

Figure 14:
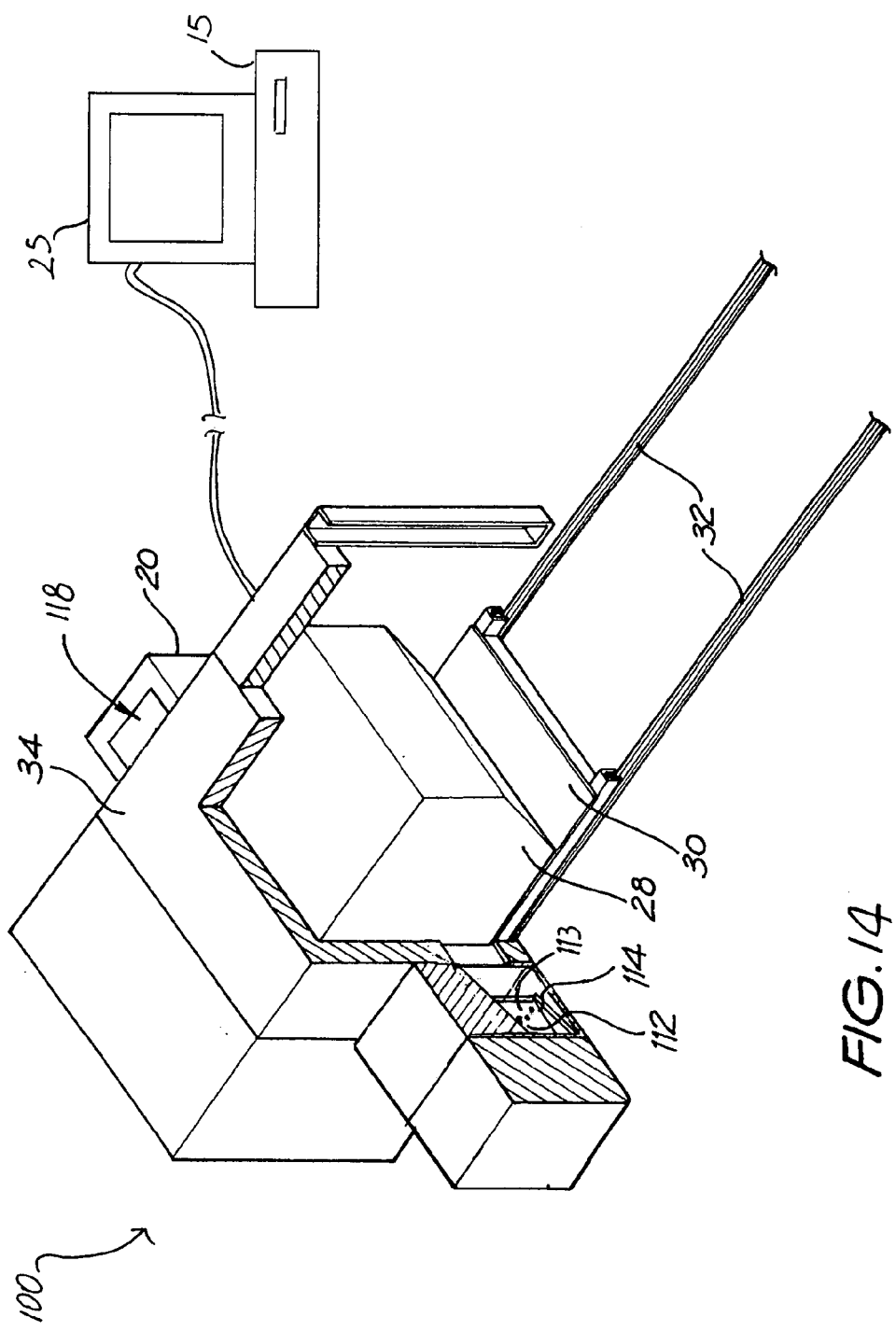
FIG. 14 is a perspective view of a further example of the radiographic equipment.

In the variation (dual neutron energy embodiment 100) as illustrated in FIG. 14, the radiation source comprises three separate generators of radiation, one producing 14 MeV neutrons 112, one producing 2.45 MeV neutrons 113, and the last producing high-energy X- or gamma-ray radiations 114. The neutron sources are sealed tube neutron generators or other compact sources of a similar nature, producing neutrons via D-T and D-D fusion reactions.

The three radiation sources are operated sequentially as the object is scanned through the analyser. In a first variation, the object is scanned through the analyser three times, with one source being operated for each scan. In a second variation, each source has a separate associated detector (desianated generally as 118) and the object is scanned only once. In a third variation, two or more of the radiation sources are operated at the same time with a single detector, and energy discrimination is used to distinguish the signals from the high energy neutrons, low energy neutrons and X- or gamma-rays.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

An, J., Xiang, X, Wu, Z., Zhou, L., Wang, L. and Wu, H., 2003. "Progress on developing $^{60}$Co container inspection systems", Applied Radiation and Isotopes 58 (2003) 315-320.

Bartle, C. M., 1995. "Method and apparatus for detecting concealed substances", U.S. Pat. No. 5,479,023 (Dec. 26, 1995).

Barzilov, A. P., Womble, P. C. and Vourvopoulos, G., 2001. "NELIS—a neutron elemental analysis system of commodities of pallets", 2001 Office of National Drug Control Policy International Symposium.

Brzosko, J. S. et al, 1992. "Advantages and limitations of 14-MeV neutron radiography", Nuclear Instruments and Methods B72 (1992) 119-131.

Buffler, A., 2001. "Contraband detection by fast neutron scattering", 2$^{nd}$ National Nuclear Technology Conference, NAC, South Africa, 13-15 May 2001, paper D-03.

Chen, G. and Lanza, R. C., 2000. "Fast neutron resonance radiography for elemental mapping", Final Research Coordination Meeting on "Bulk Hydrogen Analysis using Neutrons", Cape Town, South Africa, 23-26 Oct. 2000, pp. 31-38.

Dokhale, P. A., Csikai, J., Womble, P. C. and Vourvopoulos, G., 2001. "NELIS—an illicit drug detection system", AIP Conference Proceedings, 576 (2001) 1061-1064.

Gozani, T., 1997. "Neutron based non-intrusive inspection techniques", Proc. Internat. Conf. On Neutrons in Research and Industry, Crete, Greece, 9-15 Jun. 1996, SPIE Proceedings Series 2867 (1997) 174-181.

Hussein, E., 1992. "Detection of explosive materials using nuclear radiation: a critical review", SPIE Vol. 1736 (1992) 130-137.

Klann, R T., 1996. "Fast neutron (14.5 MeV) radiography: a comparative study", 5$^{th}$ World Conference on Neutron Radiography, Berlin, 17-20 Jun. 1996, 469-483.

Lefevre, H. W, et al, 1997. "Using a fast neutron spectrometer system to candle luggage for hidden explosives", Proc. Internat. Conf. On Neutrons in Research and Industry, Crete, Greece, 9-15 Jun. 1996, SPIE Proceedings Series 2867 (1997) 206-210.

Le Toumeur, P., Bach, P. and Dance, W. E., 1998. "Neutron fan beam source for neutron radiography purpose", 15th Int. Conf. on Applications of Accelerators in Research and Industry, Denton, Tex., USA, Nov. 4-7, 1998.

Mikerov, V. I. et al, 2000. "Investigation of prospects of fast neutron radiography on the basis of portable equipment", IAEA Coordinated Research Programme on "Bulk Hydrogen Analysis using Neutrons", Cape Town, South Africa, 23-6 Oct. 2000, Report F1-RC-655.3.

Millen, M. J., Rafter, P. T., Sowerby, B. D., Rainbow, M. T. and Jelenich, L., 1990. "Plant trial of a fast neutron and gamma-ray transmission gauge for the on-belt determination of moisture in lump coke", Nuclear Geophysics 4 (1990) 215-226.

Perion, D. et al, 2000. "System for differentiating between organic and inorganic materials", International Patent Application No. WO 00/43760.

Rynes, J. et al, 1999. "Gamma-ray and neutron radiography as part of a pulsed fast neutron analysis inspection system", Nuclear Instruments and Methods A422 (1999) 895-899.

Sawa, Z. P., Gozani, T. and Ryge, P., 1991. "Contraband detection system using direct imaging pulsed fast neutrons", U.S. Pat. No. 5,076,993, Dec. 31, 1991.

Tickner, J. R. and Sowerby, B. D., 2002. "A Detection System", Australian Provisional Patent Application No. 2002953244, Filing Date: 10 Dec. 2002.

The invention claimed is:

1. Radiographic equipment comprising:
a first neutron source of substantially mono-energetic fast neutrons produced via the deuterium-tritium or deuterium-deuterium fusion reactions, comprising a sealed-tube generator for producing the neutrons;
a source of X-rays or gamma-rays of sufficient energy to substantially penetrate an object to be imaged, the source of X-rays or gamma-rays being physically separated from the first neutron source;
a collimating block surrounding the neutron source and the X-ray or gamma-ray source, and comprising one or more slots for emitting substantially fan-shaped radiation beams;
a detector array comprising a multiplicity of individual scintillator pixels to receive neutron radiation and X-ray or gamma-ray radiation emitted from the respective sources and to convert the received radiation into light pulses, the detector array aligned with the fan-shaped radiation beams emitted from the source collimator and collimated to substantially prevent radiation other than that directly transmitted from each of the sources from reaching the array;
convertor for converting the light pulses produced in the scintillators into electrical signals;
conveyor for conveying the object between each of the sources and the detector array;
computing device for determining from the electrical signals the attenuation of the neutrons and the X-ray or gamma-ray beams and to generate output representing the mass distribution and composition of the object interposed between each of the sources and detector array; and
display for displaying images based on the mass distribution and the composition of the object being scanned.

2. Radiographic equipment according to claim 1, where the X-ray or gamma-ray source comprises a $^{137}$Cs, $^{60}$Co or similar radioisotope source having an energy of substantially 1 MeV.

3. Radiographic equipment according to claim 1, where the X-ray or gamma-ray source comprises an X-ray tube or electron accelerator producing X-rays through Bremsstrahlung on a target.

4. Radiographic equipment according to claim 1, where the neutron source produces neutrons having substantially higher energies than the X-ray or gamma-rays from the X-ray or gamma-ray source, where the neutron and X-ray or gamma-ray sources are arranged to pass through the same slot in the collimating block and a single detector array is used, comprising individual pixels of plastic or liquid organic scintillator, where discrimination between the X-rays or gamma-rays and the neutrons is made on the basis of the energy they deposit in the scintillator.

5. Radiographic equipment according to claim 1, where the sources of neutrons and X-ray or gamma-rays are arranged to pass through the same slot in the collimating block and a single detector array is used comprising individual pixels of plastic or liquid organic scintillator, where the neutron and X-ray or gamma-ray sources are operated alternately.

6. Radiographic equipment according to claim 1, where the sources of neutrons and X-ray or gamma-rays are arranged to pass through separate parallel slots in the collimator block and two detector arrays are used, one comprising individual pixels of plastic or liquid organic scintillator for the detector of the neutrons and one comprising individual pixels of plastic, liquid or inorganic scintillator for detection of the X-rays or gamma-rays.

7. Radiographic equipment according to claim 4, where each slot of the source and detector collimators are sufficiently wide to ensure full illumination of the detectors by the source, whilst minimising the detection of scattered radiation.

8. Radiographic equipment according to claim 1, further comprising a second sealed tube or similar neutron generator for producing neutrons via either the deuterium-tritium or deuterium-deuterium fusion reactions, where the second source of neutrons uses a complementary fusion reaction to the first neutron source.

9. Radiographic equipment according to claim 8, where the neutrons from the second neutron source are detected in a separate collimated detector array comprising individual pixels of plastic or liquid organic scintillator.

10. Radiographic equipment according to claim 9, where one of the first neutron source or the second neutron source has an energy of substantially 14 MeV and the other has an energy of substantially 2.45 MeV.

11. Radiographic equipment according to claim 1, where the convertor comprises a plurality of photodiodes, wherein the scintillator material is selectable to have an emission wavelength substantially matched to the response of the photodiodes.

12. Radiographic equipment according to claim 1, where the convertor comprises crossed wavelength shifting fibres coupled to a multiplicity of single or multi-anode photomultiplier tubes.

13. Radiographic equipment according to claim 11, where the electrical signals from the convertor indicate the transmission of the first neutron source and the X-rays or gamma-rays through the object being scanned, or the transmission of the neutrons from the first neutron source, the X-rays or gamma-rays and the neutrons from a second neutron source through the object being scanned.

14. Radiographic equipment according to claim 13, where mass attenuation coefficient images for each pixel are computed based on the respective transmissions and displayed with different pixel values mapped to different colours, where the image is indicative of the mass distribution and composition inferred from the computations.

15. Radiographic equipment according to claim 1, where the computing device comprises a computer to perform image processing and display the images on a computer screen.

16. Radiographic equipment according to claim 15, where the output is convertable to mass-attenuation coefficient images for each pixel for display on a computer screen with different pixel values mapped to different colours.

17. Radiographic equipment according to claim 16, where the mass-attenuation coefficient images are obtainable from count rates measured from the transmissions for each of the deuterium-tritium neutrons or deuterium-deuterium neutrons and X-rays or gamma-rays, or the deuterium-tritium neutrons, deuterium-deuterium neutrons and X-rays or gamma-rays.

18. Radiographic equipment according to claim 17, where the computer is operable to obtain cross section ratio images between pairs of mass attenuation coefficient images.

19. Radiographic equipment according to claim 18, where the proportions in which the cross section ratio images are combined are adjustable to maximise contrast and sensitivity to a particular object being examined in the image.

20. Radiographic equipment according to claim 18, where the computer is able to perform automatic material identification based on the measured cross sections.

21. Radiographic equipment according to claim 19, where the proportions in which the cross section ratio images are combined are operator adjustable.

22. Radiographic equipment according to claim 1, where the sources and the detector array are stationary and the conveyor is arranged such that the object is able to be moved in front of the source of neutrons.

23. Radiographic equipment according to claim 1, where the object is stationary and the conveyor is arranged such that the source and the detector array move in synchronicity on either side of the object.

24. Radiographic equipment according to claim 1, where multiple views are obtained by either rotating the object relative to the sources and the detector array or by rotating the sources and the detector array relative to the object.

25. Radiographic equipment according to claim 1, where the intensity of the first neutron source is of the order $10^{10}$ neutrons/second or greater.

26. Radiographic equipment according to claim 11 where the scintillators are surrounded by a mask to cover at least a portion of each of the scintillators, each mask having a first reflective surface to reflect escaped light pulses back into the scintillator.

27. The radiographic equipment according to claim 1, wherein the first neutron source has a deuteron energy of less than about 200 keV.

28. The radiographic equipment according to claim 27, wherein the deuteron energy is within a range of about 80 keV to about 110 keV.

29. The radiographic equipment according to claim 1, wherein the detector array comprises:
a first detector array comprising a plurality of scintillator pixels to receive neutron radiation emitted from the first neutron source and to convert the received neutron radiation into light pulses; and
a second detector array comprising a plurality of scintillator pixels to receive X-ray or gamma-ray radiation from the source of X-rays or gamma-rays and to convert the received X-ray or gamma-ray radiation into light pulses.

30. A radiographic equipment comprising:
a first source which produces substantially mono-energetic fast neutrons by a deuterium-tritium or deuterium-deuterium fusion reaction, the first source having a deuteron energy of less than about 200 keV;
a second source which produces X-rays or gamma-rays of a sufficient energy to substantially penetrate an object to be imaged, the second source being physically separated from the first source;
a collimating block which surrounds the first source and the second source, the collimating block comprising at least one slot, each slot for emitting substantially fan-shaped radiation beams;
a first detector array comprising a plurality of scintillator pixels for receiving neutron radiation which is emitted from the first source and passes through the object to be imaged, and for converting the received neutron radiation into first signals;
a second detector array comprising a plurality of scintillator pixels for receiving x-ray or gamma-ray radiation which is emitted from the second source and passes through the object to be imaged, and for converting the received x-ray or gamma-ray radiation into second signals;
a computing device which determines an attenuation of the mono-energetic fast neutrons and the X-rays or gamma-rays, respectively, based on the first signals and the second signals, and generates an output representing a mass distribution and composition of the object to be imaged; and
a display which displays images based on the mass distribution and the composition of the object to be imaged.

31. The radiographic equipment according to claim 30, wherein the deuteron energy is within a range of about 80 keV to about 110 keV.

* * * * *

UNITED STATES PATENT AND TRADEMARK OFFICE
CERTIFICATE OF CORRECTION

PATENT NO. : 7,313,221 B2  
APPLICATION NO. : 10/537821  
DATED : December 25, 2007  
INVENTOR(S) : Brian David Sowerby and James Richard Tickner It is certified that error appears in the above-identified patent and that said Letters Patent is hereby corrected as shown below:

Title Page:

item (73) Assigneee: Delete "Organization" and insert therefor --Organisation--.

Signed and Sealed this

Sixth Day of May, 2008

JON W. DUDAS  
*Director of the United States Patent and Trademark Office*